US009824441B2

(12) United States Patent
Satish et al.

(10) Patent No.: US 9,824,441 B2
(45) Date of Patent: Nov. 21, 2017

(54) METHOD FOR ESTIMATING A QUANTITY OF A BLOOD COMPONENT IN A FLUID CANISTER

(71) Applicant: Gauss Surgical, Inc., Los Altos, CA (US)

(72) Inventors: Siddarth Satish, Los Altos, CA (US); Kevin J. Miller, Los Altos, CA (US); Christopher Madison, Los Altos, CA (US); Andrew T. Hosford, Los Altos, CA (US); Titas De, Los Altos, CA (US); Ali Zandifar, Los Altos, CA (US); Eric Lindquist, Los Altos, CA (US); Juan Carlos Aragon, Los Altos, CA (US)

(73) Assignee: Gauss Surgical, Inc., Los Altos, CA (US)

( * ) Notice: Subject to any disclaimer, the term of this patent is extended or adjusted under 35 U.S.C. 154(b) by 242 days.

(21) Appl. No.: 14/687,842

(22) Filed: Apr. 15, 2015

(65) Prior Publication Data

US 2015/0294460 A1 Oct. 15, 2015

Related U.S. Application Data

(60) Provisional application No. 61/980,024, filed on Apr. 15, 2014, provisional application No. 62/080,927, (Continued)

(51) Int. Cl.
*G06K 9/00* (2006.01)
*G06T 7/00* (2017.01)
(Continued)

(52) U.S. Cl.
CPC ......... *G06T 7/0012* (2013.01); *G01N 21/274* (2013.01); *G06K 9/4652* (2013.01);
(Continued)

(58) Field of Classification Search
CPC  G06T 7/408; G06T 7/194; G06T 7/90; G06T 7/0014; G06T 2207/10152;
(Continued)

(56) References Cited

U.S. PATENT DOCUMENTS 2,707,955 A 5/1955 Borden
3,182,252 A 5/1965 van den Berg
(Continued)

FOREIGN PATENT DOCUMENTS

CA 2870635 A1 10/2013
CN 101505813 8/2009
(Continued)

OTHER PUBLICATIONS

Sant, et al. "Exsanguinated Blood Volume Estimation Using Fractal Analysis of Digital Images." Journal of Forensic Sciences 57.3 (2012): 610-17. Print.
(Continued)

*Primary Examiner* — Jonathan S Lee
(74) *Attorney, Agent, or Firm* — Cooley LLP

(57) ABSTRACT

A system and method for assessing the concentration of a fluid component within a container, the method comprising: receiving data associated with an image of the canister; from the image, detecting a color grid comprising color elements coupled to the canister,; selecting a region of the image corresponding to a portion of the canister; determining a match between a detected color of the region and a shade in the set of colors associated with the color grid captured in the image; based upon a position of a color element corresponding to the shade in the color grid, retrieving a concentration of the blood component associated with the shade of color.

21 Claims, 16 Drawing Sheets

Related U.S. Application Data filed on Nov. 17, 2014, provisional application No. 62/102,708, filed on Jan. 13, 2015.

(51) Int. Cl.
*G06K 9/46* (2006.01)
*G06T 7/90* (2017.01)
*G01N 21/27* (2006.01)
*A61B 10/00* (2006.01)

(52) U.S. Cl.
CPC ........ *G06T 7/90* (2017.01); *A61B 2010/0006* (2013.01); *G06T 2207/10024* (2013.01); *G06T 2207/30024* (2013.01)

(58) Field of Classification Search
CPC . G06T 2207/20072; G06T 2207/20076; G06T 2207/30024; G01N 33/49
See application file for complete search history.

(56) References Cited

U.S. PATENT DOCUMENTS

| | | |
|---|---|---|
| 3,199,507 A | 8/1965 | Kamm |
| 3,367,431 A | 2/1968 | Prindle Baker |
| 3,646,938 A | 3/1972 | Haswell |
| 3,832,135 A | 8/1974 | Chlupsa et al. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,244,369 A | 1/1981 | McAvinn et al. |
| 4,402,373 A | 9/1983 | Comeau |
| 4,422,548 A | 12/1983 | Cheesman et al. |
| 4,429,789 A | 2/1984 | Puckett |
| 4,562,842 A | 1/1986 | Morfeld et al. |
| 4,583,546 A | 4/1986 | Garde |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,132,087 A | 6/1992 | Manion et al. |
| 5,190,059 A | 3/1993 | Fabian et al. |
| 5,231,032 A | 7/1993 | Ludvigsen |
| 5,236,664 A | 8/1993 | Ludvigsen |
| 5,285,682 A | 2/1994 | Micklish |
| 5,492,537 A | 2/1996 | Vancaillie |
| 5,522,805 A | 6/1996 | Vancaillie et al. |
| 5,629,498 A | 5/1997 | Pollock et al. |
| 5,633,166 A | 5/1997 | Westgard et al. |
| 5,650,596 A | 7/1997 | Morris et al. |
| 5,709,670 A | 1/1998 | Vancaillie et al. |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,984,893 A | 11/1999 | Ward |
| 5,996,889 A | 12/1999 | Fuchs et al. |
| 6,006,119 A | 12/1999 | Soller et al. |
| 6,061,583 A | 5/2000 | Ishihara et al. |
| 6,359,683 B1 | 3/2002 | Berndt |
| 6,510,330 B1 | 1/2003 | Enejder |
| 6,640,130 B1 | 10/2003 | Freeman et al. |
| 6,641,039 B2 | 11/2003 | Southard |
| 6,728,561 B2 | 4/2004 | Smith et al. |
| 6,730,054 B2 | 5/2004 | Pierce et al. |
| 6,763,148 B1 | 7/2004 | Sternberg et al. |
| 6,777,623 B2 | 8/2004 | Ballard |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,274,947 B2 | 9/2007 | Koo et al. |
| 7,297,834 B1 | 11/2007 | Shapiro |
| 7,299,981 B2 | 11/2007 | Hickle et al. |
| 7,364,545 B2 | 4/2008 | Klein |
| 7,384,399 B2 | 6/2008 | Ghajar |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | Mccall |
| D611,731 S | 3/2010 | Levine |
| 7,670,289 B1 | 3/2010 | Mccall |
| 7,703,674 B2 | 4/2010 | Stewart |
| 7,708,700 B2 | 5/2010 | Ghajar |
| 7,711,403 B2 | 5/2010 | Jay et al. |
| 7,749,217 B2 | 7/2010 | Podhajsky |
| 7,795,491 B2 | 9/2010 | Stewart et al. |
| 7,819,818 B2 | 10/2010 | Ghajar |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,194,235 B2 | 6/2012 | Kosaka et al. |
| 8,279,068 B2 | 10/2012 | Morris et al. |
| 8,398,546 B2 | 3/2013 | Pacione et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,693,753 B2 | 4/2014 | Nakamura |
| 8,704,178 B1 | 4/2014 | Pollock et al. |
| 8,768,014 B2 | 7/2014 | Du et al. |
| 8,792,693 B2 | 7/2014 | Satish et al. |
| 8,823,776 B2 | 9/2014 | Tian et al. |
| 8,897,523 B2 | 11/2014 | Satish et al. |
| 8,983,167 B2 | 3/2015 | Satish et al. |
| 9,171,368 B2 | 10/2015 | Satish et al. |
| 9,595,104 B2 | 3/2017 | Satish et al. |
| 9,652,655 B2 | 5/2017 | Satish et al. |
| 2003/0069509 A1* | 4/2003 | Matzinger ............. G01N 33/80 600/504 |
| 2003/0095197 A1 | 5/2003 | Wheeler et al. |
| 2003/0130596 A1 | 7/2003 | Von Der Goltz |
| 2004/0031626 A1 | 2/2004 | Morris et al. |
| 2004/0129678 A1 | 7/2004 | Crowley et al. |
| 2005/0051466 A1 | 3/2005 | Carter et al. |
| 2005/0163354 A1 | 7/2005 | Ziegler |
| 2006/0058593 A1 | 3/2006 | Drinan et al. |
| 2006/0178578 A1 | 8/2006 | Tribble et al. |
| 2006/0224086 A1 | 10/2006 | Harty |
| 2007/0004959 A1 | 1/2007 | Carrier et al. |
| 2007/0024946 A1 | 2/2007 | Panasyuk et al. |
| 2007/0287182 A1 | 12/2007 | Morris et al. |
| 2008/0029416 A1 | 2/2008 | Paxton |
| 2008/0030303 A1 | 2/2008 | Kobren et al. |
| 2008/0045845 A1 | 2/2008 | Pfeiffer et al. |
| 2008/0194906 A1 | 8/2008 | Mahony et al. |
| 2009/0076470 A1 | 3/2009 | Ryan |
| 2009/0080757 A1 | 3/2009 | Roger et al. |
| 2009/0257632 A1* | 10/2009 | Lalpuria ............... G06T 7/0012 382/128 |
| 2009/0310123 A1 | 12/2009 | Thomson |
| 2009/0317002 A1 | 12/2009 | Dein |
| 2010/0003714 A1 | 1/2010 | Bachur |
| 2010/0007727 A1 | 1/2010 | Torre-Bueno |
| 2010/0025336 A1 | 2/2010 | Carter et al. |
| 2010/0027868 A1 | 2/2010 | Kosaka et al. |
| 2010/0066996 A1 | 3/2010 | Kosaka et al. |
| 2010/0087770 A1 | 4/2010 | Bock et al. |
| 2010/0280117 A1 | 11/2010 | Patrick et al. |
| 2011/0192745 A1 | 8/2011 | Min |

(56) References Cited

U.S. PATENT DOCUMENTS

| | | | |
|---|---|---|---|
| 2011/0196321 A1 | 8/2011 | Wudyka | |
| 2011/0200239 A1 | 8/2011 | Levine et al. | |
| 2011/0275957 A1 | 11/2011 | Bhandari | |
| 2011/0305376 A1 | 12/2011 | Neff | |
| 2011/0316973 A1 | 12/2011 | Miller et al. | |
| 2012/0000297 A1 | 1/2012 | Hashizume et al. | |
| 2012/0065482 A1 | 3/2012 | Robinson et al. | |
| 2012/0106811 A1 | 5/2012 | Chen et al. | |
| 2012/0210778 A1 | 8/2012 | Palmer et al. | |
| 2012/0257188 A1 | 10/2012 | Yan et al. | |
| 2012/0262704 A1 | 10/2012 | Zahniser et al. | |
| 2012/0309636 A1 | 12/2012 | Gibbons et al. | |
| 2013/0010094 A1 | 1/2013 | Satish et al. | |
| 2013/0011031 A1 | 1/2013 | Satish et al. | |
| 2013/0011042 A1 | 1/2013 | Satish et al. | |
| 2013/0034908 A1 | 2/2013 | Barstis et al. | |
| 2013/0170729 A1 | 7/2013 | Wardlaw et al. | |
| 2013/0301901 A1 | 11/2013 | Satish et al. | |
| 2013/0303870 A1 | 11/2013 | Satish et al. | |
| 2013/0308852 A1 | 11/2013 | Hamsici et al. | |
| 2014/0079297 A1 | 3/2014 | Tadayon et al. | |
| 2014/0207091 A1 | 7/2014 | Heagle et al. | |
| 2014/0294237 A1 | 10/2014 | Litvak et al. | |
| 2014/0330094 A1 | 11/2014 | Pacione et al. | |
| 2015/0310634 A1* | 10/2015 | Babcock | G01N 33/18 382/165 |
| 2016/0123998 A1* | 5/2016 | MacIntyre | A61B 5/02042 436/66 |
| 2017/0011276 A1* | 1/2017 | Mehring | G06K 9/4652 |
| 2017/0023446 A1* | 1/2017 | Rietveld | A61B 5/150358 |
| 2017/0186160 A1 | 6/2017 | Satish et al. | |

FOREIGN PATENT DOCUMENTS

| | | |
|---|---|---|
| JP | S-59-161801 U | 10/1984 |
| JP | S-62-144652 U | 6/1987 |
| JP | H06510210 A | 11/1994 |
| JP | H-11-37845 A | 2/1999 |
| JP | 2002-331031 A | 11/2002 |
| JP | 2003-075436 A | 3/2003 |
| JP | 2005-052288 A | 3/2005 |
| JP | 3701031 B2 | 9/2005 |
| JP | 2006-280445 A | 10/2006 |
| JP | 2008-055142 A | 3/2008 |
| JP | 2011-515681 A | 5/2011 |
| WO | 9217787 A1 | 10/1992 |
| WO | 9639927 A1 | 12/1996 |
| WO | WO-2009/117652 A1 | 9/2009 |
| WO | 2011019576 A1 | 2/2011 |
| WO | WO-2013/009709 A2 | 1/2013 |
| WO | WO-2013/009709 A3 | 1/2013 |
| WO | WO-2013/138356 A2 | 9/2013 |
| WO | WO-2013/138356 A3 | 9/2013 |
| WO | WO-2013/172874 A1 | 11/2013 |
| WO | WO-2013/173356 A1 | 11/2013 |
| WO | WO-2014/025415 A2 | 2/2014 |
| WO | WO-2014/025415 A3 | 2/2014 |
| WO | WO-2015/160997 A1 | 10/2015 |

OTHER PUBLICATIONS

Bellad, et al. "Standardized Visual Estimation of Blood Loss during Vaginal Delivery with its Correlation Hematocrit Changes—A Descriptive Study." South Asian Federation of Obstetrics and Gynecology 1.1 (2009): 29-34. Web.

ACOG (2012). "Optimizing protocols in obstetrics," Series 2, 25 total pages.

Adkins, A.R. et al. (2014). "Accuracy of blood loss estimations among anesthesia providers," *AANA Journal* 82(4):300-306.

Aklilu, A. Gauss Surgical Measures Blood Loss with a Smartphone. Jun. 14, 2012. <http://www.health2con.com/news/2012/06/14/gauss-surgical-measures-blood-loss-with-a-smartphone/>, 6 pages.

Al-Kadri, H.M. et al. (2014). "Effect of education and clinical assessment on the accuracy of post partum blood loss estimation," *BMC Preg. Childbirth* 14:110, 7 total pages.

AWHONN Practice Brief (2014). "Quantification of blood loss: AWHONN practice brief No. 1," AWHONN p. 1-3.

Bose, P. et al. (2006). "Improving the accuracy of estimated blood loss at obstetric haemorrhage using clinical reconstructions," *BJOG* 113(8):919-924.

Eipe, N. et al. (2006). "Perioperative blood loss assessment—How accurate?" *Indian J. Anaesth.* 50(1):35-38.

Extended European Search Report dated Apr. 1, 2015, for EP Application No. 12 810 640.8, dated Jul. 9, 2012, 8 pages.

Extended European Search Report dated Nov. 23, 2015, for EP Application No. 13 790 688.9, dated May 14, 2013, 9 pages.

Extended European Search Report dated Nov. 17, 2015, for EP Application No. 13 790 449.6, dated Jan. 10, 2013, 8 pages.

Extended European Search Report dated Nov. 4, 2016, for EP Application No. 16 183 350.4, dated Jul. 9, 2012, 9 pages.

Final Office Action dated Feb. 12, 2016, for U.S. Appl. No. 13/544,664, filed Jul. 9, 2012, 9 pages.

Final Office Action dated Aug. 26, 2016, for U.S. Appl. No. 13/894,054, filed May 14, 2013, 7 pages.

Final Office Action dated Jul. 26, 2016, for U.S. Appl. No. 14/876,628, filed Oct. 6, 2015, 5 pages.

Habak, P.J. et al. (2016). "A comparison of visual estimate versus calculated estimate of blood loss at vaginal delivery," *British J. Med. Medical Res.* 11(4):1-7.

Holmes, A.A. et al. (2014). "Clinical evaluation of a novel system for monitoring surgical hemoglobin loss," *Anesth. Analg.* 119(3):588-594.

International Search Report dated Sep. 17, 2012, for PCT Application No. PCT/US2012/045969, dated Jul. 9, 2012, 2 pages.

International Search Report dated Sep. 24, 2013, for PCT Application No. PCT/US2013/040976, dated May 14, 2013, 2 pages.

International Search Report dated Mar. 26, 2013, for PCT Application No. PCT/US2013/021075, dated Jan. 10, 2013, 2 pages.

International Search Report dated Jul. 24, 2015, for PCT Application No. PCT/US2015/026036, dated Apr. 15, 2015, 2 pages.

International Search Report dated Mar. 30, 2017, for PCT Application No. PCT/US2016/068540, dated Dec. 23, 2016, 3 pages.

Jones, R. (2015). "Quantitative measurement of blood loss during delivery," *AWHONN* p. S41.

Kamiyoshihara, M. et al. (2008). "The Utility of an Autologous Blood Salvage System in Emergency Thoracotomy for a Hemothorax After Chest Trauma," *Gen. Thorac. Cardiovasc. Surg.* 56:222.

Lyndon, A. et al. (2010). "Blood loss: Clinical techniques for ongoing quantitative measurement," *CMQCC Obstetric Hemorrhage Toolkit*, pp. 1-7.

Lyndon, A. et al. (2015). "Cumulative quantitative assessment of blood loss," *CMQCC Obstetric Hemorrhage Toolkit Version* 2.0, pp. 80-85.

Manikandan, D. et al. (2015). "Measurement of blood loss during adenotonsillectomy in children and factors affecting it," *Case Reports in Clinical Medicine* 4:151-156.

Merck for Mother's Program (2012). Blood loss measurement: Technology opportunity assessment, 9 total pages.

Non-Final Office Action dated Aug. 13, 2015, for U.S. Appl. No. 13/544,664, filed Jul. 9, 2012, 8 pages.

Non-Final Office Action dated Aug. 2, 2016, for U.S. Appl. No. 13/544,664, filed Jul. 9, 2012, 6 pages.

Non-Final Office Action dated May 9, 2014, for U.S. Appl. No. 13/544,679, filed Jul. 9, 2012, 7 pages.

Non-Final Office Action dated Mar. 30, 2016, for U.S. Appl. No. 13/894,054, filed May 14, 2013, 9 pages.

Non-Final Office Action dated Sep. 5, 2014, for U.S. Appl. No. 13/738,919, filed Jan. 10, 2013, 8 pages.

Non-Final Office Action dated Mar. 20, 2015, for U.S. Appl. No. 14/613,807, filed Feb. 4, 2015, 8 pages.

Non-Final Office Action dated Dec. 15, 2015, for U.S. Appl. No. 14/876,628, filed Oct. 6, 2015, 8 pages.

Non-Final Office Action dated Apr. 20, 2017, for U.S. Appl. No. 13/894,054, filed May 14, 2013, 7 pages.

(56) References Cited

OTHER PUBLICATIONS

Notice of Allowance dated May 12, 2014, for U.S. Appl. No. 13/544,646, filed Jul. 9, 2012, 10 pages.
Notice of Allowance dated Sep. 3, 2014, for U.S. Appl. No. 13/544,679, filed Jul. 9, 2012, 8 pages.
Notice of Allowance dated Nov. 10, 2014, for U.S. Appl. No. 13/738,919, filed Jan. 10, 2013, 10 pages.
Notice of Allowance dated Jun. 25, 2015, for U.S. Appl. No. 14/613,807, filed Feb. 4, 2015, 10 pages.
Notice of Allowance dated Oct. 26, 2016, for U.S. Appl. No. 14/876,628, filed Oct. 6, 2015, 11 pages.
Notice of Allowance dated Feb. 15, 2017, for U.S. Appl. No. 13/544,664, filed Jul. 9, 2012, 10 pages.
Pogorelc, D. iPads in the OR: New Mobile Platform to Monitor Blood Loss During Surgery. MedCityNews, Jun. 6, 2012. http://medcitynews.com/2012/06/ipads-in-the-or-new-mobile-platform-to-monitor-blood-loss-during-surgery, 4 pages.
Roston, A.B. et al. (2012). "Chapter 9: Blood loss: Accuracy of visual estimation," in *A comprehensive textbook of postpartum hemorrhage: An essential clinical reference for effective management*, $2^{nd}$ edition, Sapiens publishing, pp. 71-72.
Schorn, M.N. (2010). "Measurement of blood loss: Review of the literature," *J. Midwifery and Women's Health* 55(1):20-27.
Sukprasert, M. et al. (2006). "Increase accuracy of visual estimation of blood loss from education programme," *J. Med. Assoc. Thai* 89(suppl. 4):S54-S59.
Written Opinion of the International Searching Authority dated Sep. 17, 2012, for PCT Application No. PCT/US2012/045969, dated Jul. 9, 2012, 4 pages.
Written Opinion of the International Searching Authority dated Sep. 24, 2013, for PCT Application No. PCT/US2013/040976, dated May 14, 2013, 4 pages.
Written Opinion of the International Searching Authority dated Mar. 26, 2013, for PCT Application No. PCT/US2013/021075, dated Jan. 10, 2013, 6 pages.
Written Opinion of the International Searching Authority dated Jul. 24, 2015, for PCT Application No. PCT/US2015/026036, dated Apr. 15, 2015, 6 pages.
Written Opinion of the International Searching Authority dated Mar. 30, 2017, for PCT Application No. PCT/US2016/068540, dated Dec. 23, 2016, 8 pages.
U.S. Appl. No. 15/416,986, filed Jan. 26, 2017, by Satish et al.
U.S. Appl. No. 15/390,017, filed Dec. 23, 2016, by Satish et al.
U.S. Appl. No. 15/594,017, filed May 12, 2017, by Satish et al.
Extended European Search Report dated Jul. 26, 2017, for EP Application No. 15 780 653.0, filed on Apr. 15, 2015, 12 pages.

* cited by examiner

QR CODE CORNER EXTRACTION

PALETTE EXTRACTION

ROI EXTRACTION

METHOD FOR ESTIMATING A QUANTITY OF A BLOOD COMPONENT IN A FLUID CANISTER

CROSS-REFERENCE TO RELATED APPLICATIONS

This application claims the benefit of U.S. Provisional Application Ser. No. 61/980,024, filed on 15 Apr. 2014, U.S. Provisional Application Ser. No. 62/080,927, filed on 17 Nov. 2014, and U.S. Provisional Application Ser. No. 62/102,708, filed on 13 Jan. 2015, which are each incorporated herein in its entirety by this reference.

TECHNICAL FIELD

This invention relates generally to the surgical field, and more specifically to a new and useful method for estimating a quantity of a blood component in a canister for use in surgical practice.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. First Method

Figure 1A:
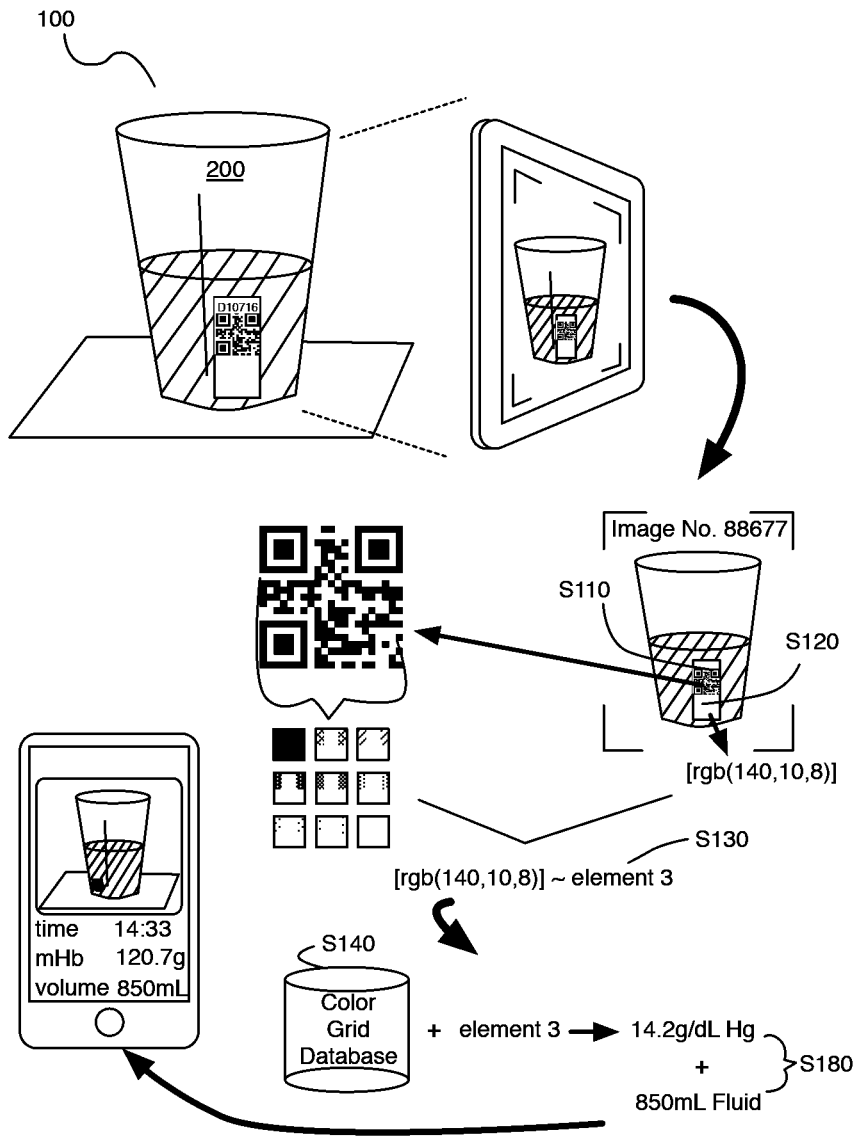
FIGS. 1A and 1B depict flowchart representations of an embodiment of a method for estimating a quantity of a fluid component.
Figure 1B:
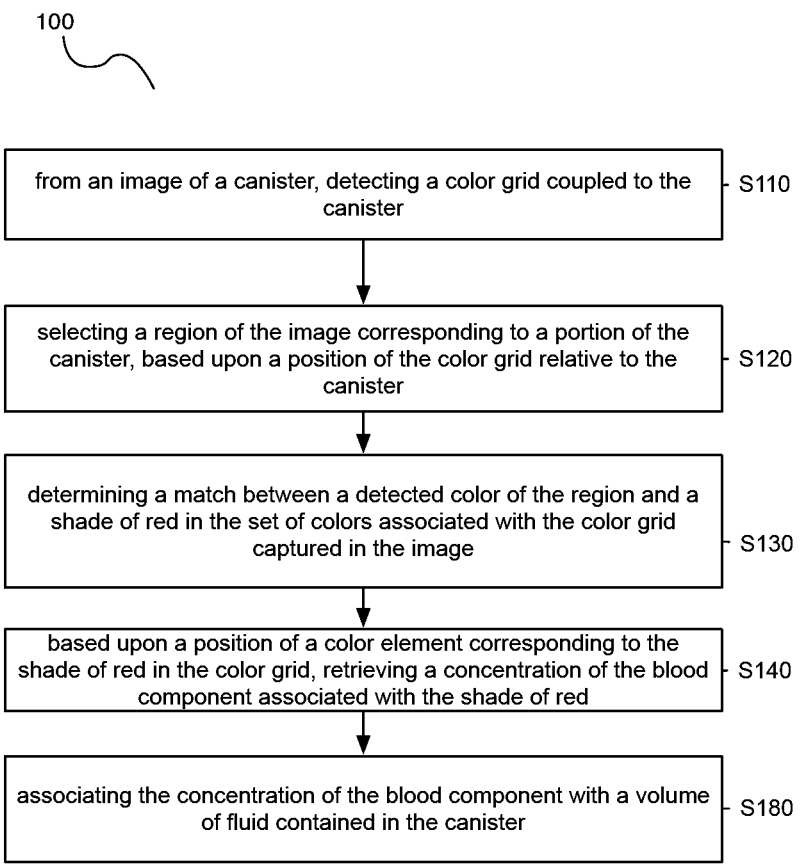

As shown in FIGS. 1A and 1B, a method 100 for estimating a quantity of a blood component in a canister comprises: from an image of a canister, detecting a color grid coupled to the canister S110, the color grid comprising an array of color elements, wherein each color element is associated with at least one of a set of colors in a red spectrum; selecting a region of the image corresponding to a portion of the canister, based upon a position of the color grid relative to the canister S120; determining a match between a detected color of the region and a shade of red in the set of colors associated with the color grid captured in the image S130; based upon a position of a color element corresponding to the shade of red in the color grid, retrieving a concentration of the blood component associated with the shade of red S140; and associating the concentration of the blood component with a volume of fluid contained in the canister S180, thereby estimating the quantity of the blood component in the canister.

Generally, the method functions to implement machine vision to estimate the content of a blood component within a fluid canister. In particular, the method 100 analyzes an image of a fluid canister to identify a color grid printed on, applied to, or otherwise coupled to the canister, to color match a particular shade in the color grid to a region of the image corresponding to the canister, and to estimate a concentration of a blood component (e.g., red blood cells, hemoglobin, free hemoglobin, etc.) within the canister based on a blood component concentration empirically determined and associated with the particular shade. The method can further determine a total volume of fluid within the canister and combine this volume with the estimated concentration of the blood component to calculate a total amount (e.g., mass, volume, or weight) of the blood component within the canister.

In a specific application, the method 100 can be used to estimate a mass of hemoglobin within a fluid canister present in a clinical/medical environment, wherein the fluid canister is used for blood salvage during a procedure, and wherein fluid within the canister includes at least some blood (e.g., in addition to saline and/or other bodily fluids of a patient). In relation to this specific application and variations thereof, the surface of the fluid canister, without implementation of the method 100, can be prone to specular reflections/glare and variations in ambient light can lead to variations in color of fluid within the fluid canister. As such, the method 100 includes implementation of steps and components that function to mitigate specular reflections and glare, as well as steps and components that mitigate effects of variations in ambient lighting.

The method 100 can therefore implement methods and techniques described in U.S. application Ser. No. 13/544,646 entitled "System and Method for Estimating Extracorporeal Blood Volume in a Physical Sample" and filed on 9 Jul. 2012, U.S. application Ser. No. 13/894,054 entitled "System and Methods for Managing Blood Loss of a Patient" and filed on 14 May 2013, U.S. application Ser. No. 13/738,919 entitled "System and Method for Estimating a Quantity of a Blood Component in a Fluid Canister" and filed on 10 Jan. 2013, and U.S. application Ser. No. 14/072,625 entitled "Method for Triggering Blood Salvage" and filed on 5 Nov. 2013, which are each incorporated herein in its entirety by this reference.

The blood component can be any of whole blood, red blood cells, hemoglobin, platelets, plasma, white blood cells, analytes, or any other suitable blood component or combination of blood components. Furthermore, the blood component can comprise any component derived from any of the above blood components (e.g., intracellular content, molecular content, etc.). The method can additionally or alternatively implement similarly techniques to estimate a concentration (and an amount) of a non-blood component within the canister, such as saline, ascites, bile, irrigant saliva, gastric fluid, mucus, pleural fluid, interstitial fluid, urine, fecal matter, or any other bodily fluid of a patient.

The fluid canister can be a suction canister implemented in a surgical or other medical, clinical, or hospital setting to collect blood and other bodily fluids. For example, the canister can include a surgical fluid canister defining a translucent polymer vessel including a series of fluid volume indicator markings (e.g., horizontal indicator markings) arranged vertically along a wall of the vessel and visible from outside the container. The canister can alternatively be a blood salvage canister, an intravenous fluid bag, or any other suitable blood- or fluid-bearing container for collecting surgical waste or recovering biological fluid. The fluid canister is also transparent, translucent, or includes a transparent or translucent region along a wall (e.g., vertical wall, slanted wall) of the container such that an image of the canister can include sufficient information to enable the method 100 to color match fluid contained in the fluid canister to a color shade printed onto, applied onto, or otherwise associated with the canister, and to accordingly estimate a concentration of the blood component within the canister.

The method 100 can therefore be useful in quantifying an amount and/or a concentration of a blood component (e.g., hemoglobin) and/or other fluids (e.g., saline) contained within a fluid canister through non-contact means and in real-time, such as during a surgery or other medical event. A patient's blood loss and euvolemia status can then be tracked according to these data, such as described in U.S. patent application Ser. No. 14/072,625. However, the method 100 can be applicable in any other scenario or environment to estimate a concentration and/or amount of a blood component or other fluid or particulate in a vessel.

The method 100 can thus be implemented by a computer system as a fluid canister analyzer that analyzes a photographic image (e.g., digital image) of a canister to estimate the quality of a fluid contained therein. The computer system can be cloud-based (e.g., Amazon EC2), a mainframe computer system, a grid-computer system, or any other suitable computer system. For example, the method 100 can be implemented by a handheld (e.g., mobile) computing device, such a smartphone, a digital music player, or a tablet computer executing a native blood component analysis application, such as shown in FIG. 1A. For example, an image acquisition module integral with the computing device can capture the image of the fluid canister, and a processor integral with the computing device can implement Blocks of the method 100 to extract information indicative of the quality of the fluid in the canister from the image. The computing device can additionally or alternatively communicate with a remote server, such as over the Internet via a wireless connection, the server can perform one or more Blocks of the method, 100 and one or more outputs of the method 100 can be transmitted from the remote server back to the computing device for further analysis and/or subsequent presentation to an entity (e.g., a nurse, an anesthesiologist). The computing device can also include or can be coupled to a digital display, and the method 100 can present information to the entity through the display.

Alternatively, the method 100 can be implemented as a standalone blood volume estimation system including a fluid canister, a fluid canister stand, an image acquisition module, a camera stand configured to support a camera of the image acquisition module adjacent the fluid canister, a digital display, a processor configured to perform at least a portion of the method, and/or a communication module configured to communicate with a remote server that performs one or more Blocks of the method 100. In this implementation, the camera can be substantially non-transiently positioned relative to a fluid canister stand such that the camera remains in a suitable position to capture an image of a canister substantially throughout a surgery or other medical event and/or until the canister is full. The blood volume estimation system can thus regularly capture and analyze images of the fluid canister, such as every thirty seconds or every two minutes. The blood volume estimation system can further communicate (e.g., via Bluetooth) with another one or more systems implementing any of the methods described in U.S. application Ser. Nos. 13/544,646, 13/894,054, 13/738,919, and 14/072,625 to form a fluid management system for generating a substantially comprehensive analysis of one or more of: extracorporeal blood volume, total patient blood loss, patient euvolemia status, and any other suitable patient state in a clinical or non-clinical environment. However, the method 100 can be implemented in or by any other suitable computer system, computing device, or combination thereof.

Furthermore, variations of the method 100 and system can be adapted to process image data (or other data) derived from any other suitable fluid receiver (e.g., canister, test strip, absorbent pad, surgical textile, sponge, fluid receiving bag, drape, cell salvage system, drain device, etc.) associated with or otherwise coupled to a color grid (e.g., incorporated into a quick response code, incorporated into a barcode, incorporated into a rectilinear array, incorporated into an axially symmetric array, etc.), wherein the fluid receiver is configured to receive (e.g., receive into a cavity, receive upon absorption) a volume of fluid (e.g., urine, saline, ascites, bile, irrigant saliva, gastric fluid, mucus, pleural fluid, interstitial fluid, fecal matter, non-biological fluid, etc.). As such, variations of the method 100 and color grid 300 described below can facilitate mitigation of ambient light effects in an environment of the fluid receiver, in determining a concentration and/or an amount of a fluid component within a volume of fluid received at the fluid receiver.

2. Color Grid, Canister, and Processing Module

Figure 2A:
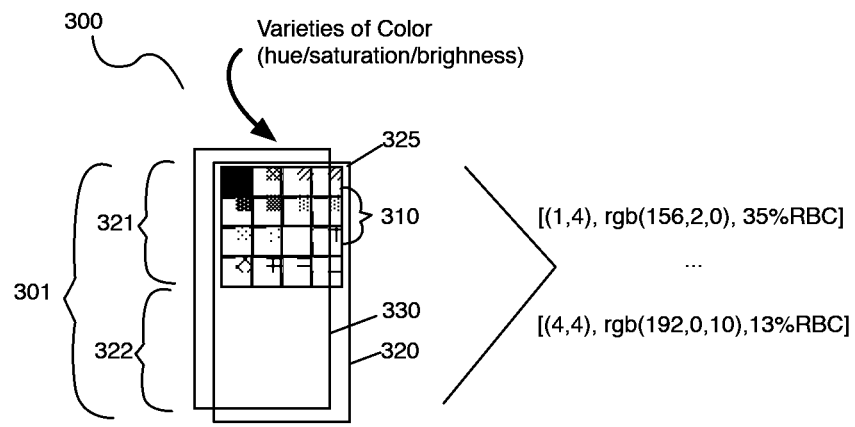
FIGS. 2A, 2B, and 2C are schematic representations of a color grid of an embodiment of a method and system for estimating a quantity of a fluid component.

As shown in FIG. 2A, in one embodiment, the color grid 300 includes an array of color elements 310 (e.g., regions comprising one or more "pixels") of distinct colors, wherein the array of color elements is printed, applied, projected onto, or otherwise coupled to an exterior surface of the canister. In one example, the color grid 300 is applied in the form of a decal 301 onto the canister 200. In this example, the decal 301 can include: an adhesive layer 320; an opaque layer 325 arranged over a first portion 321 of the adhesive layer 320; an array of color elements 310, each of a discrete shade of red, arranged over the opaque layer 325; and an anti-glare layer 330 laminated over the array of color elements 310 and directly over a second portion 322 of the adhesive layer 320 adjacent the first portion 321. The adhesive layer 320 is preferably substantially transparent in order to allow a color of fluid within the canister 200 to be accurately represented in image data of the canister-color grid assembly; however, the adhesive layer 320 can alternatively have any characteristic color (e.g., shade, hue, saturation, intensity, opacity, etc.) in order to facilitate image processing (e.g., color correction) of an image including the color grid 300.

In this example, the color grid 300 can then be applied (i.e., "stuck") over an exterior surface of the canister 200 by a manufacturer before shipping the canister to an end-user, or can alternatively be coupled to a canister by a nurse, anesthesiologist, or other end-user before or during a surgery or other medical event. However, variations of the specific example of the color grid 300 can omit one or more of: the adhesive layer 320, the opaque layer 325, and the anti-glare layer 330 (e.g., in relation to a fluid receiver that has a matte finish or otherwise does not produce glare), and can additionally or alternatively include any other suitable layers that enhance or otherwise facilitate image processing of an image of the color grid within a field of view.

The opaque layer 325 of the color grid 300 functions to provide a repeatable background for the color grid 300, such that perceived (or imaged) colors of shades in the color grid are not substantially affected by lighting conditions, reflections of other onto the color grid 300 or canister, or an opacity of fluid contained within an adjacent canister (or other object). In specific examples, the opaque layer 325 can include one or more of: an aluminum sheet, a foil sheet, a white-enameled copper sheet, and any other suitable material that provides an opaque region for the color grid 300.

The anti-glare layer 330 of the color grid 300 functions to reduce or substantially eliminate glare over the color grid 300 and an adjacent region of fluid in an image of the canister 200 such that the image contains sufficient color data to enable the method 100 to correlate a color of the fluid in the image with a blood component concentration (or similarly to enable the variations of the method 100 described below to color normalize the image and to correlate a color of the fluid in the image with a concentration of the blood component). The anti-glare layer 330 can further function to maintain a consistent surface treatment across both the color grid and a translucent or transparent surface of canister 200, such that a portion of an image of the canister 200 corresponding to fluid contained therein can be color normalized and/or matched to a particular shade in the color grid 300 to estimate a concentration of the blood component within the canister 200. In one specific example, the anti-glare layer 330 can extend beyond a portion of the color grid 300 comprising the array of color elements 310, thus producing a region 6 of the fluid canister 200, immediately adjacent to the array of color elements, that is coupled to the anti-glare layer 330. The region 6 can thus be used, for instance, as in Block S120 of the method 100, for analysis and eventual estimation of the amount of the blood component present within the fluid canister 200. The region 6 can, however, be defined relative to a position of the color grid 300 on the canister 200 in any other suitable manner.

In a few such alternative variations, the color grid 300 can be arranged on a placard adjacent the canister 200, on a work (e.g., table) surface adjacent the canister 200, on a canister 200 stand supporting the canister 200, on a surgical glove near or contacting the canister 200, or on any other surface near the canister 200 such that the color grid 300 and the canister 200 can be imaged together.

The array of color elements 310 of the color grid 300 includes multiple varieties of a color (i.e., hue characterized by a wavelength of light) that is characteristic of the blood component (i.e., red), wherein the varieties of the color are differentiated according to one or more of value/brightness (e.g., in terms of shade or tint) and saturation/chroma. Variations of the array of color elements 310 can, however, include multiple hues of color. Furthermore, the colors of the array of color elements 310 of the color grid 300 can be described in RGB triplet format (e.g., in terms of intensities of red, green, and blue components), hexadecimal format (i.e., hex format), and/or any other suitable format that facilitates downstream processing of information derived from the array of color elements 310 at a computing system. The colors of the array of color elements 310 can further exist within any suitable color space (e.g., Adobe RGB color space, CIE 1931 XYZ color space, CIE L*a*b color space, etc.) in relation to printing of the color grid 300, projection of colors of the color grid 300, perception of colors of the color grid 300, and/or any other suitable factor.

In one variation, the array of color elements 310 of the color grid 300 can include a set of red elements spanning hex color values in the #xx0000 range (e.g., from #200000 to #FF0000) or spanning RGB color values in the rgb(x,0,0) range (e.g., from (32,0,0) to (255,0,0)). However, in this variation, the color grid 300 can additionally or alternatively represent any other suitable color (e.g., in terms of hue, saturation/chroma, brightness/value) that may be substantially near a color of a bloodied (i.e., blood-containing) fluid. In the example shown in FIG. 2A, each color in the color grid 300 can be represented as an element arranged in a grid format wherein each element is of substantially uniform shade (i.e., having a low degree of variability across pixels of the color element).

In the example shown in FIG. 2A, the color grid 300 includes a rectilinear grid layout of elements in which each element represents a unique color brightness (i.e., shade or tint) of a color (e.g., red) within the set of colors. In this example, the elements can be arranged with substantially similar color nearby to yield a relatively smooth color transition across the color grid 300 in one or more linear directions. In another example, the color grid can include multiple elements representing the same color shade. In this example, the array of color elements 310 can be arranged with colors having specific characteristics (e.g., brightness, saturation, etc.) forming a pattern across the color grid 300. In more detail, a set of elements of the same (dark) shade of red can form a cross centered in a square color grid 300 and split the color grid 300 into four quadrants, and additional elements can fill the first quadrant with increasingly lighter shades of red nearing the far corner of the first quadrant. In this example, the first quadrant can be mirrored vertically, diagonally, and horizontally into the second, third, and fourth quadrants of the color grid, respectively, thus allowing the color grid 300 to be less affected by orientation (e.g., in relation to 90° rotations of the color grid). In a variation of this example, the color grid 300 can be axially symmetric (e.g., using a circular or otherwise axially symmetric array of color elements), thus allowing the color grid 300 to be even less affected by orientation (e.g., of the canister, of the color grid relative to the canister). The color grid 300 can, however, comprise or omit any suitable axis of symmetry.

Figure 2B:
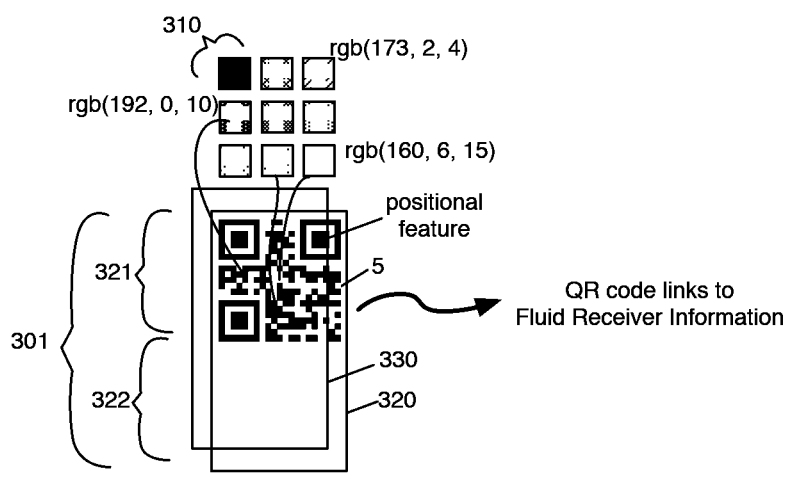

In an implementation similar to the above example, with a rectilinear array of color elements 310, the color grid 300 contains colored blocks of various discrete colors (e.g., red hues, saturation of red hues, intensity of red hues, etc.) arranged in a matrix barcode 5 (e.g., a Quick Response or "QR" code, another optical machine-readable barcode, etc.), as shown in FIG. 2B. In this implementation, the set of colored blocks—along with a set of white blocks (e.g., interspersed white blocks)—can be arranged in a square grid pattern printed on or otherwise applied to a sticker (or decal, etc.), wherein information including one or more of: alignment information, position information, version information, identification information, and any other suitable information is encoded within the square grid pattern based on the (relative) positions of colored and white blocks therein. A device can thus implement machine vision techniques according to blocks of the method 100 described herein to account for distortion of the matrix barcode 5 (e.g., due to a non-planar surface of the canister 200), to extract color information from color elements of the color grid 300 for application to a color of fluid within the images canister on which the sticker (or decal) is applied (or printed); the device can also decode the grid pattern of the color grid to retrieve additional information related to the color grid and/or to the canister. In this implementation, information accessible upon decoding of the matrix barcode 5 can be at least partially redundant with other information printed or otherwise provided (e.g., printed) on a surface of the color grid 300. For instance, the color grid 300 can include a region with printed text describing an alphanumeric identifier of the fluid canister 200, and the alphanumeric identification can also be accessible upon decoding of the matrix barcode 5. Thus, in relation to a set of canisters (i.e., for multiple patients, for a single patient within a medical environment), a color grid 300 can be used to uniquely identify a canister, while still including a set of color elements (i.e., in unique configurations) that is substantially similar across the set of canisters.

Figure 3A:
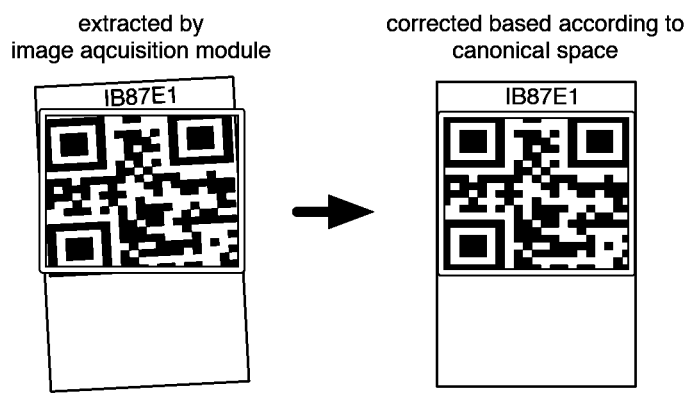
FIGS. 3A-3F depict variations of blocks in an embodiment of a method and system for estimating a quantity of a fluid component.

In a first example that implements a color grid 300 with encoded information, a scanning device of the mobile computing device (e.g., optical sensor module of a mobile computing device) can be configured to locate one or more positional features (e.g., QR-code corner features) of the color grid 300, to extract an identifier (e.g., alphanumeric identifier) of the canister 200 from the matrix barcode 5, and to transmit the identifier and the image data of the canister to a processing module (e.g., computing system, server) in communication with the mobile computing device (or other image acquisition device). The processing module can then use the identifier to determine one or more characteristics of the canister (e.g., morphological characteristics, make, model, serial number, geometry, maximum internal volume, wall thickness, and/or surface glossiness, etc.) and to reconstruct a template of how the color grid would look (i.e., without distortion) in a known configuration (e.g., canonical space, with a certain orientation, distance, and perspective relative to an optical sensor). In particular, the template of how the color grid looks in canonical form can be derived from an electronic file used to print the color grid, wherein the electronic file represents the configuration of the color grid without any warping or distortion, and wherein the electronic file is retrieved by the processing system upon reception of the identifier. The processing module can then be configured to identify an undistorted configuration of the color grid 300 based upon positional adjustment of the one or more positional features of the color grid 300 relative to the template, as shown in FIG. 3A.

Figure 3B:
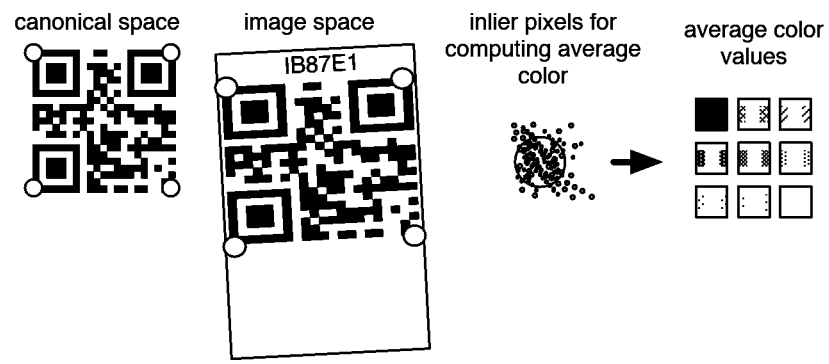

In the first example, the processing module can comprise a palette extraction module configured to use the identifier (e.g., alphanumeric identifier) of the canister to define masks of a set of regions of the array of color elements 310 of the color grid 300 in canonical space, and to use the one or more positional features (e.g., extracted QR-code corners) to fit a transformation model (e.g., homography) between canonical space and image space associated with the image data. The transformation model can then be used, by the processing system, to transform each of the set of regions into image space. Then, for each of the set of regions, a set of pixels of an associated transformed mask can be processed to determine an average (e.g., median, mean) color value (i.e., RGB color value, hex color value) as representative of the associated region, as shown in FIG. 3B. As such, the processing module can extract color values of the array of color elements 310 of the color grid 300 in a manner that is consistent across all color grids for a set of canisters. In the first example, the set of regions comprises 9 regions, each representing a distinct color value; however, in variations of the specific example, the set of regions can alternatively comprise any other suitable number of regions for normalization of the image (e.g., in relation to ambient light conditions) and/or extraction of blood component information from the image.

Figure 3C:
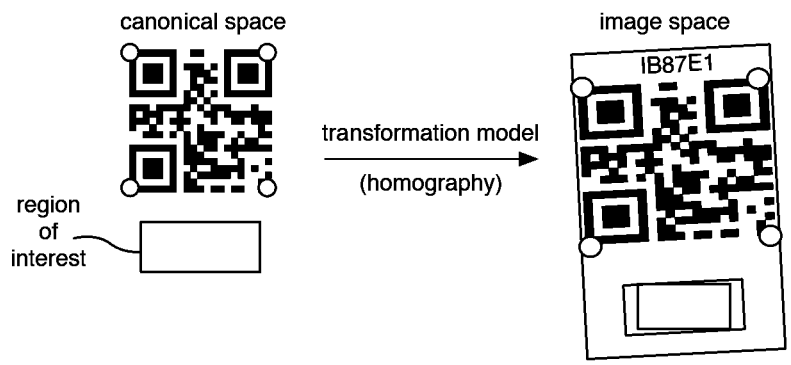
Figure 3D:
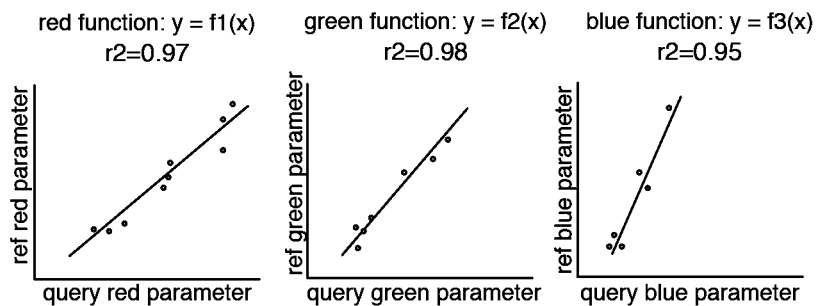
Figure 3D:

Then, in the first example, the processing module can be configured to identify a region of the canister 200 for determination of the amount of the blood component (e.g., hemoglobin mass), wherein the region is captured in the image data and associated with a position of the color grid 300 on the canister 200. The processing module can then be configured to use the transformation model (e.g., homography) to transform the region of the canister 200 from canonical space into image space, and to inscribe a bounding region inside the region, as shown in FIG. 3C. In the first example, the processing system can then be configured to normalize the image data to account for effects of ambient light based upon a reference palette of the array of color elements 310, wherein the reference palette includes a representation of the array of color elements 310 in a specific configuration (e.g., derived from a reference image with controlled light conditions, derived from color information used to print the array of color elements, etc.). In the first example, the reference palette can be used to normalize the set of regions of the color palette output by the palette extraction module according to a set of fit functions that transform red channel, green channel, and blue channel color information values captured in the set of regions of the color palette into normalized red channel, green channel, and blue channel values, thereby outputting a normalized color palette that is normalized for ambient light conditions, as shown in FIG. 3D.

Figure 3E:
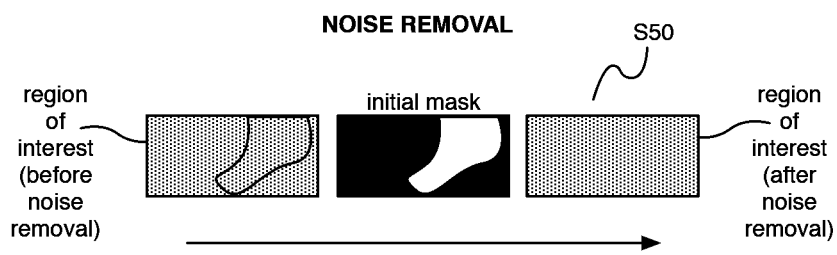

In the first example, the processing system is then configured to remove noise or other artifacts (e.g., artifacts caused by air bubbles under the color grid 300, artifacts caused by debris between the color grid 300 and the canister, etc.) from the image data of the region of interest for blood component analysis, wherein in a specific example, artifact removal is performed according to a maximally stable extremal regions (MSER) algorithm to determine an initial mask of substantially artifact-less subregions of the region of interest, as shown in FIG. 3E. Then, the processing system is configured to remove any pixels whose color value is significantly different from a median color value of pixels of the initial mask, in order to remove aberrations present after implementation oft the MSER algorithm. The processing system can additionally or alternatively implement a Laplacian of Gaussian algorithm, a difference of Gaussians algorithm, and/or a determinant of Hessian algorithm to remove noise or other artifacts.

Figure 3F:
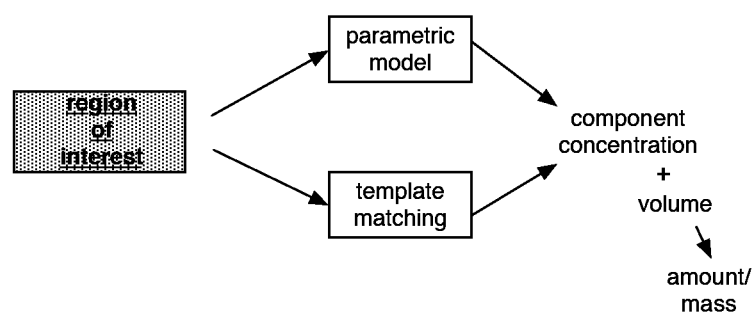

Finally, the processing system is configured to determine an estimated hemoglobin mass from the region of interest of the canister, based upon a parametric model. In particular, the parametric model implements a support vector machine (SVM) algorithm with a radial basis function (RBF) kernel that generates a hemoglobin concentration derived from red value, green value, and blue value color intensities the region of interest, and multiplies the hemoglobin concentration by the volume of fluid within the canister can to determine the estimated hemoglobin mass. Additionally or alternatively, as shown in FIG. 3F, any other suitable parametric model (e.g., linear regression model, power curve driven regression model, other regression model, etc.) or a non-parametric model can be implemented by the processing system to determine an amount of any other suitable blood component within the canister (or other fluid receiver), as described in one or more of: U.S. application Ser. Nos. 13/544,646, 13/894,054, 13/738,919, and 14/072,625.

Additionally or alternatively, variations of the above system and method can incorporate multiple color grids coupled to a canister (or other fluid receiver), in order to enable correction of location-dependent ambient lighting effects, in characterizing fluid at the canister (or other fluid receiver). For instance, a first color grid positioned at a first location on the canister and a second color grid positioned at a second location on the canister can be used to correct effects caused by differences in the way ambient light hits the first location and the second location of the canister.

Figure 4:
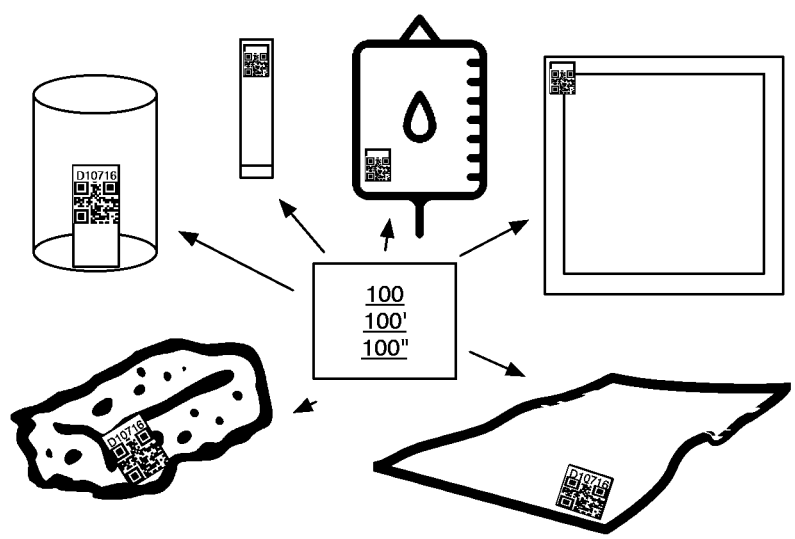
FIG. 4 depicts variations of fluid receivers used in adaptations of an embodiment of a method and system for estimating a quantity of a fluid component.

As shown in FIG. 4, variations of the above example of a system can also be adapted to process image data (or other data) derived from any other suitable fluid receiver (e.g., canister, test strip, absorbent pad, surgical textile, sponge, fluid receiving bag, drape, cell salvage system, drain device, etc.) associated with or otherwise coupled to a color grid (e.g., incorporated into a matrix barcode, incorporated into a quick response code, incorporated into a barcode, incorporated into a rectilinear array, incorporated into an axially symmetric array, etc.), wherein the fluid receiver is configured to receive (e.g., receive into a cavity, receive upon absorption) a volume of fluid (e.g., urine, saline, ascites, bile, irrigant saliva, gastric fluid, mucus, pleural fluid, interstitial fluid, fecal matter, etc.). As such, variations of the system above can facilitate mitigation of ambient light effects in an environment of the fluid receiver, in determining a concentration and/or an amount of a fluid component within a volume of fluid received at the fluid receiver.

In another example that implements a color grid 300 with encoded information, a scanning device can extract manufacturer, supplier, batch number, serial number, version, hospital, a uniform resource locator ("URL") or other web address, and/or any other suitable information—pertaining to the canister 200 and/or to the color grid 300—from the matrix barcode 5 by: identifying positions of white (or other light-colored) blocks and positions of dark (e.g., red) blocks in an image of the matrix barcode 5 captured by the device; identifying position markers (e.g., QR-code corners) within the matrix barcode 5; determining an orientation of the matrix barcode based on relative locations of the position markers; identifying a set of modules within the matrix barcode based on the orientation of the matrix barcode 5; decoding each module into a character based on the orientation of the matrix barcode and positions of light blocks and dark (e.g., red) blocks within each module; and assembling characters extracted from the set modules into a meaningful resource. In this example, the device can assemble the characters into a URL and retrieve data related to the canister and/or the color grid from the URL via a network (e.g., Internet) connection, such as make, model, serial number, geometry, maximum internal volume, wall thickness, and/or surface glossiness, etc. of the canister onto which the sticker (with the matrix barcode 5) is applied. The device can additionally or alternatively access the URL extracted from the matrix barcode 5 to retrieve color template data for the matrix barcode 5, such as hemoglobin concentration, red blood cell concentration, and/or hemolysis proportion, etc. corresponding to each color represented by colored blocks in the color grid; the device can then implement template matching techniques described herein to match a color of a portion the image corresponding to fluid in the canister to a particular color represented in the color grid shown in the same image and apply hemoglobin concentration, red blood cell concentration, and/or hemolysis proportion, etc. corresponding to the particular color—as specified in the color template data retrieved from the URL—to an estimate for qualities of fluid contained in the canister, as described below. However, the color grid can include any other number of shades of red (or other hue) arranged in any other suitable way.

In the foregoing examples, each particular color value represented in the color grid 300 can be used to facilitate image normalization in consideration of ambient light effects, and/or be paired with a specific blood component concentration. For example, fluid solutions containing saline and 0.0%, 2.5%, 5.0%, 7.5% . . . 92.5%, 95.0% red blood cells by volume can be prepared in various fluid containers, each fluid container including a substantially identical color grid with an array of elements of various shades of red. In this example, an image of each fluid solution can be imaged, and, for each fluid solution, a color of the fluid solution extracted from the corresponding image and the color of the solution matched to one color element (or to two nearest color elements) in the color grid. Each color value represented in the color grid 300 can thus be matched to and associated with a particular red blood cell concentration in saline. Thus, during a subsequent surgery or other medical event, the method can reverse this procedure to extract a color from a region of an image of a fluid canister corresponding to bloodied fluid, to match this color to a color element in the color grid applied to the canister, and to estimate a red blood cell concentration of the fluid within the canister based on the red blood cell concentration associated with the selected color element.

Figure 2C:
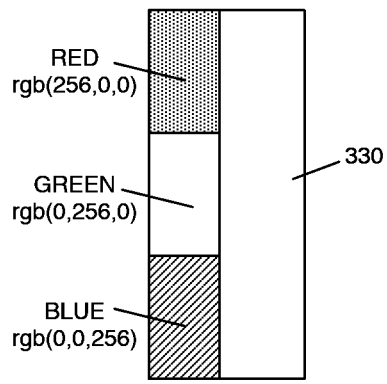

In another implementation, the color grid includes elements representing multiple pure colors, such as red, blue, and green, such as shown in FIG. 2C. In this implementation, the method can color normalize an image of the canister 200 by adjusting a red, blue, green, contrast, brightness, and/or other color or image parameter to match portions of an image corresponding to the color elements to a know color value of each of these elements (e.g., rgb(256, 0,0), rgb(0,0,256), and rgb(0,256, 0)), as described below. However, the color grid 300 can include any other number of shades of any other color arranged in any other suitable way.

The color grid 300 can also include one or more reference points (e.g., positional features) of known size, geometry, and/or spacing, and one or more blocks of the method 100 can implement machine vision techniques to identify the reference point(s) in an the image of the canister and to scale, rotate, translate, skew, and/or transform the image to match the identified reference point(s) in the image to its known (i.e., true) size, geometry, and/or spacing. For example, the color grid 300 can include one or more printed symbols, such as a series of corner or "+" symbols arranged about the colored elements. Alternatively, the elements can be of a specific size and geometry (e.g., 3 mm×3 mm square elements), which one or more Blocks of the method 100 can identify in an image of the canister and implement to transform the image, to extract a dimension from the image, and/or to locate a point of interest (e.g., a particular color element in the color grid) in the image.

3. Template Matching

Block S110 recites: from an image of a canister, detecting a color grid coupled to the canister, the color grid comprising an array of color elements, wherein each color element is associated with at least one of a set of colors in a red spectrum, and Block S120 of the method recites selecting a region of the image corresponding to a portion of the canister, based upon a position of the color grid relative to the canister.

Generally, once an image of the canister is captured, (e.g., as described in U.S. patent application Ser. No. 13/738,919), Block S110 can comprise implementing machine vision techniques to identify the color grid in the image, and/or one or more positional features (e.g., QR-code corners) associated with the color grid in the image, examples and variations of which are described above in relation to the processing system. Block S110 can comprise implementing one or more of: object localization, segmentation (e.g. edge detection, background subtraction, grab-cut-based algorithms, etc.), gauging, clustering, pattern recognition, template matching, feature extraction, descriptor extraction (e.g. extraction of texton maps, color histograms, HOG, SIFT, etc.), feature dimensionality reduction (e.g. PCA, K-Means, linear discriminant analysis, etc.), feature selection, thresholding, positioning, color analysis, parametric regression, non-parametric regression, unsupervised or semi-supervised parametric or non-parametric regression, and any other type of machine learning or machine vision to identify the color grid (or a portion of or a symbol on the color grid) in the image.

Block S110 can also comprise implementing machine vision techniques to identify each discrete color element of an array of color elements in the color grid in the image and to extract a color characteristic for each identified color element. For example, for one identified example color element, Block S110 can comprise determining an average color value (e.g., a hex color value, an rgb( ) color value) of each pixel corresponding to one color element in the image. In one variation, Block S110 can comprise defining masks of a set of regions, each region associated with a color element of the array of color elements in canonical space, and using one or more positional features (e.g., extracted QR-code corners) to fit a transformation model (e.g., homography) between canonical space and image space associated with the image. Block S110 can then comprise using the transformation model to transform each of the set of regions into image space and then, for each of the set of regions, processing a set of pixels of an associated transformed mask to determine an average (e.g., median, mean) color value (i.e. RGB color value, hex color value) as representative of the color element. Block S110 can then comprise storing these values with the image, such as in the form of virtual overlay of color values over corresponding color elements in the color grid in the image. As such, Block S110 can enable extraction of color values of the array of color elements of a color grid in a manner that is consistent across all color grids for a set of canisters. Variations and examples of color element identification are described above in relation to the palette extraction module of the processing system described above.

Block S110 can further comprise assigning an address to each color element in the color grid in the image, such as in the form of a (m, n) matrix coordinate system for a the color grid that includes a rectilinear array of color elements. For example, in a 10×10 color grid array with one hundred color elements, Block S110 can address a top-left element at (1,1), an element immediately to the right of the top-left element (2,1), and a bottom right element (100, 100). Block S110 can also comprise determining an orientation of the color grid in the image, such as based upon one or more positional features (e.g., associated with a position of a make, model, or serial number printed on the decal), and assigning addresses to the color elements in the image accordingly. Block S110 can then group each determined color value of a color element in the image with a corresponding color grid address, such as in the form ((m,n),#XXXXXX).

With the color grid thus identified in the image, Block S120 can comprise selecting a particular region of the image to match to a color in the color grid. For example, as described above, the color grid can be incorporated into a decal including a transparent region with an anti-glare surface adjacent the color grid, Block S110 can then comprise analyzing the image to determine an orientation of the color grid on the canister, and Block S120 can comprise selecting a region of the image adjacent a particular edge of the color grid and corresponding to the transparent region of the decal based on the determined orientation (and size) of the color grid in the image. In this example, the decal can be rectangular, and the color grid can be square and arranged over one half and on one side of the decal, Block S110 can comprise detecting a longitudinal axis and a lateral axis of the decal, and Block S120 can comprise selecting a group or cluster of pixels—in the image—grouped around the longitudinal axis of the decal on a half of the decal opposite the color grid. Alternatively, the decal can define an elongated anti-glare strip arranged vertically along a side of the canister, and Block S120 can comprise identifying a surface of fluid in the canister (as described in U.S. application Ser. Nos. 14/072,625 and/or 13/738,919) and select a linear group of pixels in the image corresponding to the anti-glare surface, distinct from the color grid applied to the canister, and running from a lowest point on the decal up to the identified surface of the fluid. However, Block S120 can comprise selecting any other region of the image in any other suitable way.

Block S130 recites: determining a match between a detected color of the region and a shade of red in the set of colors associated with the color grid captured in the image. Generally, Block S130 implements machine vision techniques to match a color of the particular region selected in Block S120 to a color of a particular color element in the color grid coupled to the canister and captured in the image.

In one implementation, Block S130 includes calculating a mean color value (e.g., a hex color value, an RGB color value) from a color value of each pixel in the region of the image selected in Block S120. Block S130 can alternatively comprise calculating a color value for each pixel or for each subgroup of pixels in the region selected in Block S120 can then identify a median color value in the selected region. However, Block S130 can comprise calculating and/or assigning a particular color value to the region of the image corresponding to fluid in the canister in any other suitable manner. Once the region of the image containing data corresponding to fluid within the canister is thus quantified, Block S130 can comprise comparing the color value of this region to determined color values of the color elements in the color grid in the image. In particular, Block S130 can comprise comparing the color value of the region to color values calculated for the color elements in Block S110, and selecting a particular color element of color value nearest that of the selected region. Alternatively, Block S130 can comprise selecting two color elements corresponding to two color values nearest the color value of the selected region.

Block S130 can then comprise passing this nearest color value or these two nearest color values—or one or more color grid address(es) associated with the nearest color value(s)—to Block S140 and/or Block S150 of the method 100. Thus, though color information captured in one image of the canister and the color grid may differ from color information captured in one another of the canister and the color grid (and from an image of another canister and another color grid), Block S130 can enable matching of two (or more) colors represented in the image. In particular, because the two matched colors were captured under the same lighting, shadow, ISO, shutter speed, sampling rate aperture, and other conditions affecting recordation of light (i.e., color), this color match may be inherently normalized for all such lighting and imaging conditions.

Block S140 recites: based upon a position of a color element corresponding to the shade of red in the color grid, retrieving a concentration of the blood component associated with the shade of red. Generally, Block S140 functions to assign known concentrations of the blood component to particular color elements in the color grid in the image. In one implementation, as described above, Block S110 identifies a particular type, make, or model of the color grid on the imaged canister by implementing optical character recognition (OCR) (or any other machine vision technique) to read a QR-code, SKU number, a bar code, or a model number, etc. of the color grid from the image, and Block S140 comprises passing this identifier to a remote color grid database. In this implementation, Block S140 receives a set of color grid addresses with corresponding known (i.e., empirically-determined) blood component concentrations and then maps the known blood component concentrations to respective color elements in the color grid based on the addresses assigned to the color elements and the addresses received from the color grid database. For example, Block S140 can append the element address and color value coordinates to read in the form ((m,n),#XXXXXX , y % V). Thus in the example, one dark reddish-brown element in the color grid can be assigned the coordinate ((5,6),#200000, 67.5% V) and a light washed-out pink element in the color grid can be assigned the coordinate ((2,1),#FFCCCC, 5.0% V). Block S140 can thus cooperate with Block S110 to compile a list of coordinates, each specifying a location of an element in the color grid, a color value of the element in the image (which may differ amongst various images of the same canister), and a corresponding blood component concentration.

In another implementation, Block S110 comprises extracting an identifier of the color grid in the image, Block S140 comprises selecting a computer file of model color element addresses and known blood component concentrations and extracting a single blood component concentration corresponding to the (real) color element address selected in Block S130. Similarly, for two color element addresses received from Block S130, Block S140 can comprise selecting two corresponding blood component concentrations and then passing these values to Block S150. However, Block S140 can function in any other way to collect known blood component concentration data corresponding to one or more color elements in the color grid.

Block S180 recites: associating the concentration of the blood component with a volume of blood contained in the canister, thereby estimating the quantity of the blood component in the canister. Generally, Block S180 functions to assign a known concentration of the blood component associated with a particular color element to the fluid in the canister, based upon a color match between a corresponding color element and a color of the fluid. In one implementation, Block S180 comprises applying the matched color value or the selected color element address to the list of coordinates that specify color element locations, color values, and corresponding blood component concentrations, and outputting a single blood component concentration for the fluid contained in the canister shown in the image. In another implementation, Block S180 comprises receiving two blood component concentrations—corresponding to two color elements in the color grid nearest the fluid color shown in the image—from Block S140 and averaging these blood component concentrations to generate a final estimate of the blood component concentration of fluid in the imaged canister. In a similar implementation, Block S180 can comprise comparing a distance (e.g., in a hex color system) between the (average) color of the region of image selected in Block S120 (and corresponding to fluid in the image) and the colors of the nearest color elements of the color grid selected in Block S140. In this implementation, Block S180 can then comprise applying these color distances to the color values to interpolate the blood component concentration in the canister. For example, Block S130 can extract color value rgb(130,2,2) from the region selected in Block S120 and cooperate with Block S140 to select color element addresses ((8,4), rgb(128,0,3), 47.5% V) and ((7,5), rgb(136, 0,1), 45.0% V) as nearest the selected region color. In this example, Block S180 can thus implement linear interpolation to estimate that the actual red blood cell concentration in the canister is approximately 45.6% by volume. However, Block S180 can comprise estimating the concentration of red bloods cells or any other blood component in the canister in any other suitable manner.

Block S180 can then comprise displaying this estimated concentration value, such as on a display or other user interface arranged within the operating room, as described in U.S. patent application Ser. No. 14/072,625, and/or pass this concentration value to Block S192 for estimation of an amount (e.g., a weight, a volume, a mass) of the blood component in the canister based upon a volume of fluid within the canister, as described further below.

Furthermore, as noted above, variations of the method 100 can be adapted to process image data (or other data) derived from any other suitable fluid receiver (e.g., canister, test strip, absorbent pad, surgical textile, sponge, fluid receiving bag, drape, cell salvage system, drain device, etc.) associated with or otherwise coupled to a color grid (e.g., incorporated into a quick response code, incorporated into a barcode, incorporated into a rectilinear array, incorporated into an axially symmetric array, etc.), as shown in FIG. 4, wherein the fluid receiver is configured to receive (e.g., receive into a cavity, receive upon absorption) a volume of fluid (e.g., urine, saline, ascites, bile, irrigant saliva, gastric fluid, mucus, pleural fluid, interstitial fluid, fecal matter, etc.). In particular, color elements of the color grid, as described above, can comprise any other suitable (e.g., non-red) color(s) configured to facilitate image data normalization for environmental condition effects, and/or for extraction of relevant fluid component characteristics (e.g., concentrations, purities, etc.) from a volume of fluid at the fluid receiver.

Figure 5:
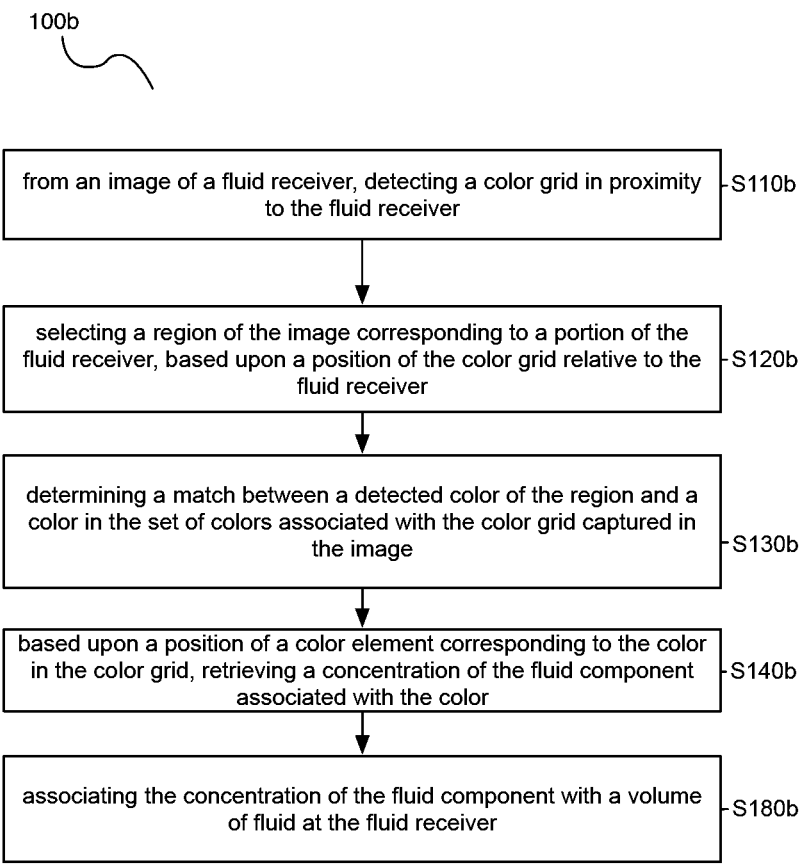
FIG. 5 depicts a flowchart representation of a variation of a method and system for estimating a quantity of a fluid component.

In one such variation, as shown in FIG. 5, a method 100b can comprise: from an image of a fluid receiver, detecting a color grid in proximity to the fluid receiver Snob, the color grid comprising an array of color elements, wherein each color element is associated with at least one of a set of colors; selecting a region of the image corresponding to a portion of the fluid receiver, based upon a position of the color grid relative to the fluid receiver S120b; determining a match between a detected color of the region and a color in the set of colors associated with the color grid captured in the image S130b; based upon a position of a color element corresponding to the color in the color grid, retrieving a concentration of a fluid component associated with the color S140b; and associating the concentration of the fluid component with a volume of fluid contained in the canister S180, thereby estimating the quantity of the fluid component in the canister.

As such, variations of the method 100 can facilitate mitigation of ambient light effects (and other effects) in an environment of the fluid receiver, in determining a concentration and/or an amount of a fluid component within a volume of fluid received at the fluid receiver.

4. First Variation—Image Normalization and Concentration Extraction

Figure 6A:
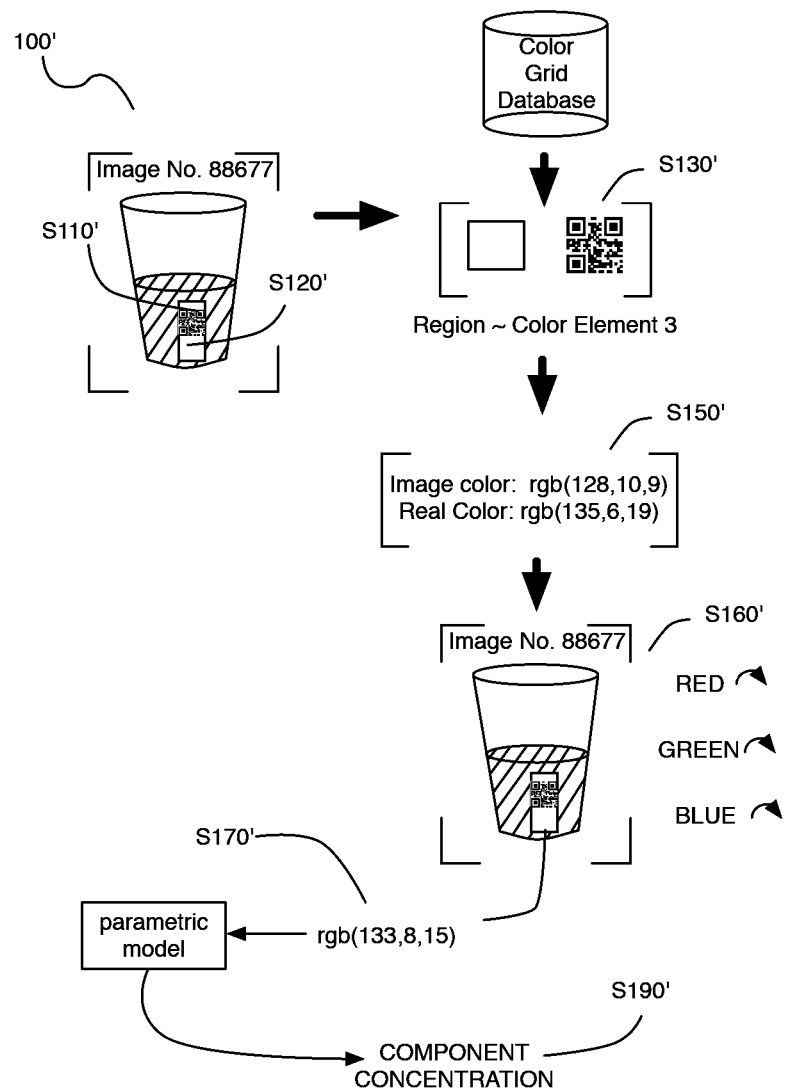
FIGS. 6A-6C depict variations of a method for estimating a quantity of a fluid component.
Figure 6B:
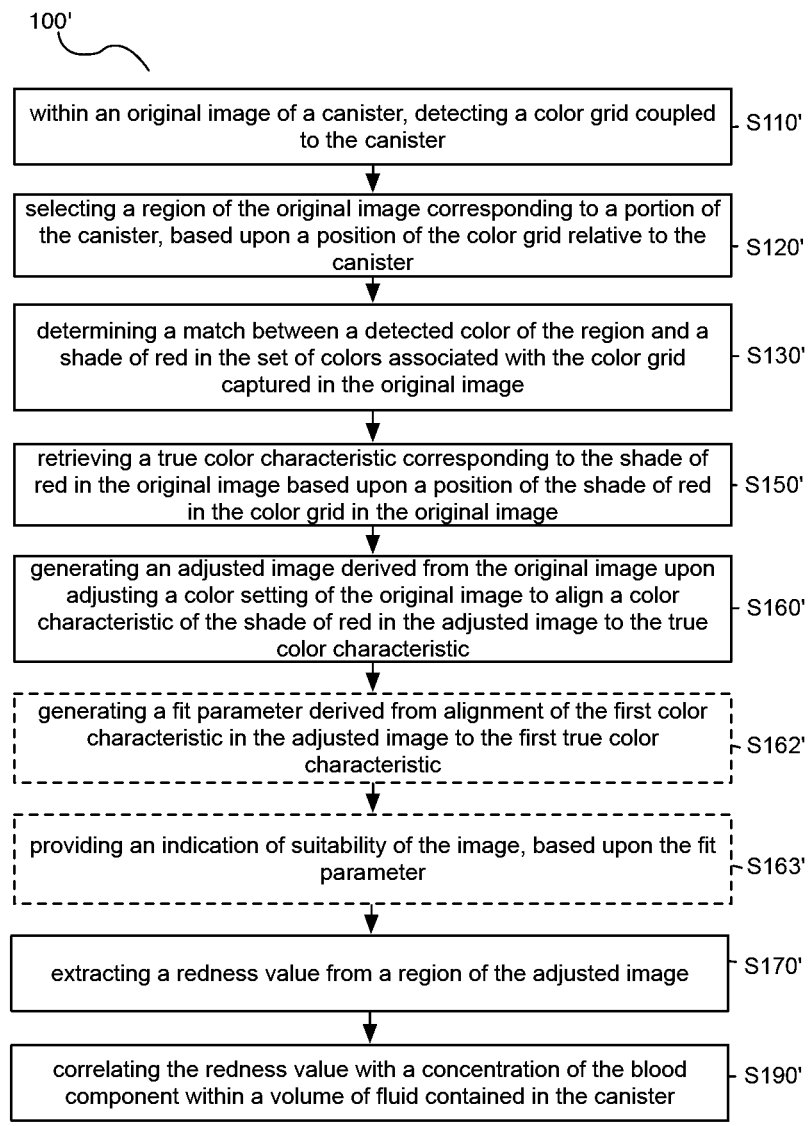

As shown in FIGS. 6A and 6B, a first variation of the method 100' includes: within an original image of a canister, detecting a color grid coupled to the canister S110', the color grid comprising an array of color elements, wherein each color element is associated with at least one of a set of colors in a red spectrum; selecting a region of the original image corresponding to a portion of the canister, based upon a position of the color grid relative to the canister S120'; determining a match between a detected color of the region and a shade of red in the set of colors associated with the color grid captured in the original image S130'; retrieving a true color characteristic corresponding to the shade of red in the original image based upon a position of the shade of red in the color grid in the original image S150'; generating an adjusted image derived from the original image upon adjusting a color setting of the original image to align a color characteristic of the shade of red in the adjusted image to the true color characteristic S160'; extracting a redness value from a region of the adjusted image S170'; and correlating the redness value with a concentration of the blood component within a volume of fluid contained in the canister S190'.

Generally, this variation of the method 100' functions to match a color in a region of the image corresponding to fluid in the canister, to a particular color represented in one or more elements in the color grid. This variation of the method 100 further functions to normalize the image by adjusting at least one of: a red component (e.g., intensity), a blue component (e.g., intensity), a green component (e.g., intensity), contrast, brightness, and any other suitable color or image parameter to match the particular color element in the image to a known color property of a reference color element in a reference color grid (e.g., a color grid imaged under controlled environmental conditions, etc.). In this variation, once the image is thus normalized, the method 100 can implement a parametric model to extrapolate a blood component concentration from the region of the image corresponding to the fluid in the canister. This variation of the method 100 can be performed by the processing system described in Section 2 above, but can additionally or alternatively be implemented using any other suitable system.

In particular, Block S150' recites: retrieving a true color characteristic corresponding to the shade of red in the original image based on a position of the particular shade of red in the color grid in the original image. Block S150' can thus comprise implementing a method or technique similar to Block S140' described above to retrieve a real or known color value of a color element (or a subset of color elements) selected in the image in Block S130'. For example, Block S150' can retrieve this color information from local memory on a mobile computing device (e.g., a tablet, a smartphone) executing the method 100 or from a remote color grid database.

Block S160' recites: generating an adjusted image from the original image upon adjusting a color setting of the original image to align a color characteristic of the shade of red in the adjusted image to the true color characteristic. Generally, once the reference color value for the selected color element is collected, Block S160' can include adjusting at least one of: a red component (e.g., intensity), a blue component (e.g., intensity), a green component (e.g., intensity), contrast, brightness, and any other suitable color or image parameter to match the color value of the selected color element in the image to the reference color value of the color element. For example, if Block S130' selects a color element with the address ((4,9), rbg(156,8,9)) but the reference color value of the color element in row 4, column 9 of the color grid is rgb(150, 0, 12), Block S160' can include decreasing a red component of the image, decrease a green component of the image, and increase a blue component of the image until the color value of the (4,9) color element reaches rgb(150, 0, 12).

In another implementation, for two color elements selected in Block S130', Block S160' can include implementing similar functionality as described above in relation to Block S140' to interpolate a target color value between the real color values of the two selected color elements, and Block S160' can then adjust the image color properties accordingly.

Furthermore, Block S160' can include generating a fit parameter derived from alignment of the first color characteristic in the adjusted image to the first true color characteristic S162'; and providing an indication of suitability of the image, based upon the fit parameter S163' (e.g., providing an indication at a display of a mobile computing device in communication with the computer system). In particular, the fit parameter can be derived from one or more functions fit between a true color characteristic (e.g., red intensity, blue intensity, green intensity) and a color characteristic derived from the original image, wherein the fit parameter can include one or more of: an r-value of a line fit, a parameter derived from outlier detection in relation to a fitted function, and any other suitable fit parameter. This aspect of Block S160' can thus be used as a quality control step that enables a user or other entity associated with the volume of fluid to be informed of unsuitable image data acquired of the canister and/or the color grid (e.g., in relation to scuffing of the color grid, marking of the color grid, or any other suitable image artifact that renders the image unsuitable for processing).

Block S170' recites: extracting a redness value from a region of the adjusted image, and Block S190' of this variation of the method recites: correlating the redness value with a concentration of the blood component within fluid contained in the canister. Generally, once the image is color normalized, Block S170' and Block S190' cooperate to implement a parametric model or algorithm to convert the normalized color of the selected region in the adjusted image—corresponding to fluid in the canister—into a blood component concentration, as described in U.S. patent application Ser. No. 14/072,625. As such, Blocks S170' and S190' can include selecting a region of the adjusted image corresponding to a portion of the canister, based upon a position of the color grid relative to the canister; determining a concentration of the blood component from a set of color parameters (e.g., red color intensity, green color intensity, and blue color intensity) derived from the region of the adjusted image (e.g., based upon a parametric model, based upon template matching, etc.); and determining an amount of the blood component within the canister, based upon determining a volume of fluid within the canister. Blocks S170' and/or S190' of the first variation of the method 100' can, however, be implemented in any other suitable manner.

Furthermore, as noted above, variations of the method 100' can be adapted to process image data (or other data) derived from any other suitable fluid receiver (e.g., canister, test strip, absorbent pad, surgical textile, sponge, fluid receiving bag, drape, cell salvage system, drain device, etc.) associated with or otherwise coupled to a color grid (e.g., incorporated into a quick response code, incorporated into a barcode, incorporated into a rectilinear array, incorporated into an axially symmetric array, etc.), wherein the fluid receiver is configured to receive (e.g., receive into a cavity, receive upon absorption) a volume of fluid (e.g., urine, saline, ascites, bile, irrigant saliva, gastric fluid, mucus, pleural fluid, interstitial fluid, fecal matter, etc.). In particular, color elements of the color grid, as described above, can comprise any other suitable (e.g., non-red) color(s) configured to facilitate image data normalization for environmental condition effects, and/or for extraction of relevant fluid component characteristics (e.g., concentrations, purities, etc.) from a volume of fluid at the fluid receiver.

Figure 6C:
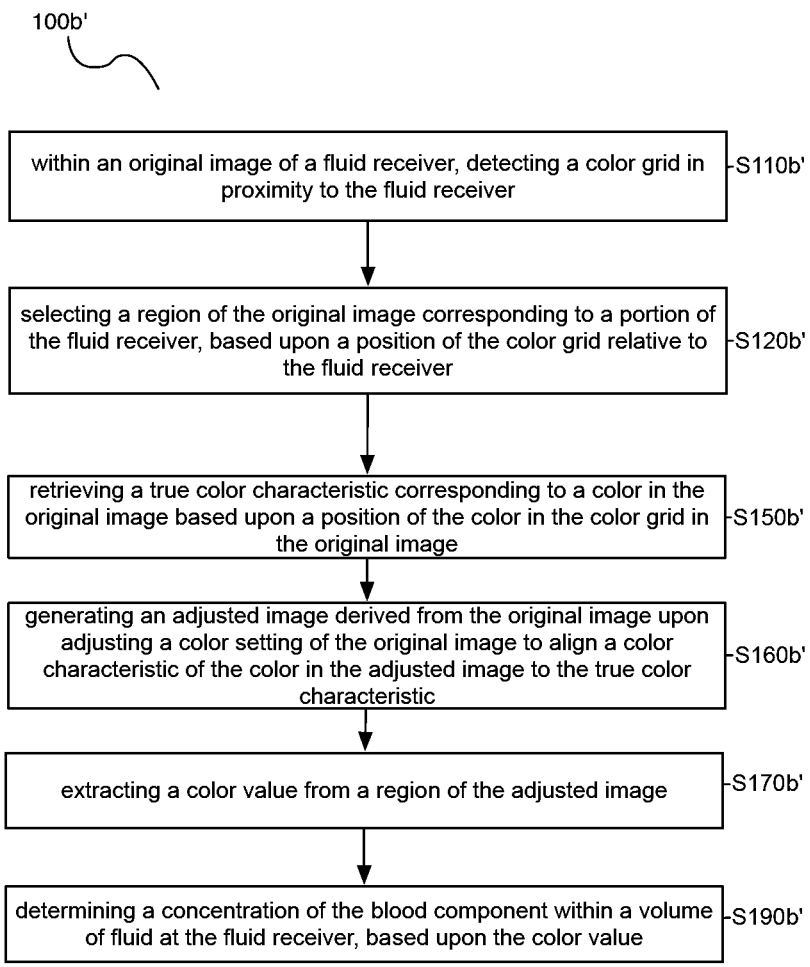

In one such variation, as shown in FIG. 6C, a method 100b' can include: within an original image of a fluid receiver, detecting a color grid in proximity to the fluid receiver S110b', the color grid comprising an array of color elements, wherein each color element is associated with at least one of a set of colors; selecting a region of the original image corresponding to a portion of the fluid receiver, based upon a position of the color grid relative to the fluid receiver S120b'; retrieving a true color characteristic corresponding to a color in the original image based upon a position of the color in the color grid in the original image S150b'; generating an adjusted image derived from the original image upon adjusting a color setting of the original image to align a color characteristic of the color in the adjusted image to the true color characteristic S160b'; extracting a color value from a region of the adjusted image S170b'; and determining a concentration of the blood component within a volume of fluid at the fluid receiver, based upon the color value S190b'.

As such, variations of the method 100' can facilitate mitigation of ambient light effects (and other effects) in an environment of the fluid receiver, in determining a concentration and/or an amount of a fluid component within a volume of fluid received at the fluid receiver.

5. Second Variation

Figure 7A:
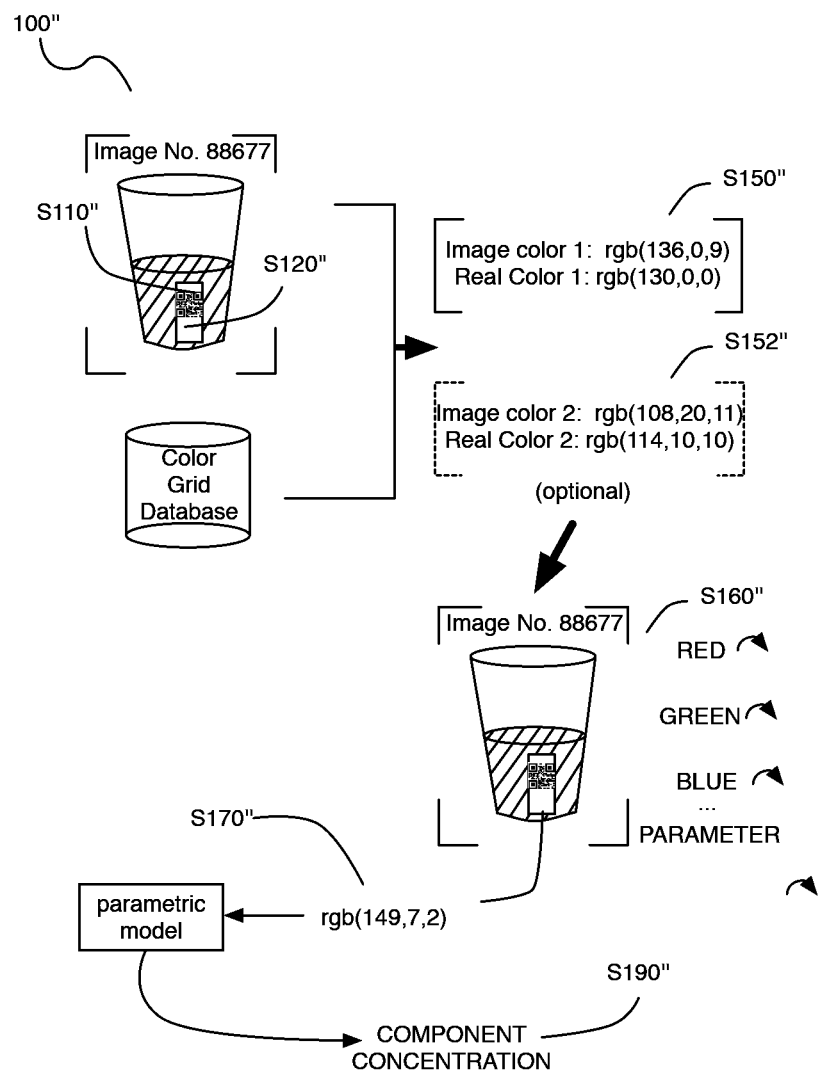
FIGS. 7A-7C depict variations of a method for estimating a quantity of a fluid component.
Figure 7B:
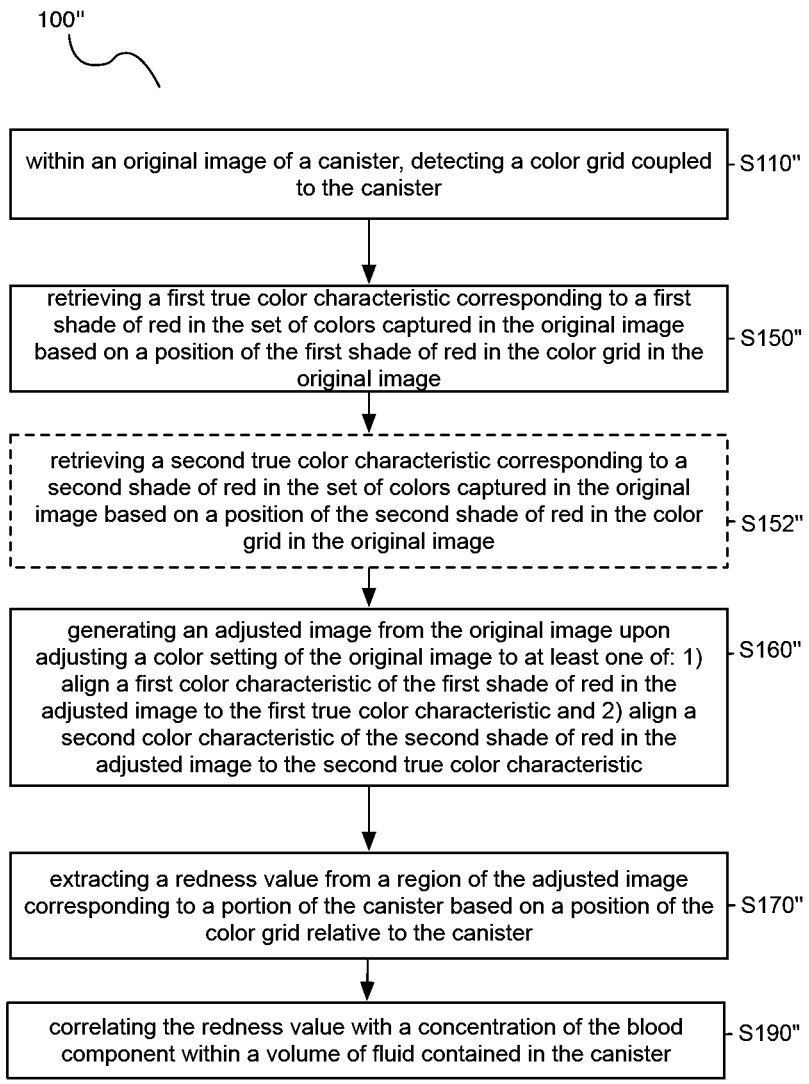

As shown in FIGS. 7A and 7B, a second variation of the method 100" includes: within an original image of a canister, detecting a color grid coupled to the canister S110", the color grid comprising an array of color elements, wherein each color element is associated with at least one of a set of colors in a red spectrum; retrieving a first true color characteristic corresponding to a first shade of red in the set of colors captured in the original image based on a position of the first shade of red in the color grid in the original image S150"; retrieving a second true color characteristic corresponding to a second shade of red in the set of colors captured in the original image based on a position of the second shade of red in the color grid in the original image S152"; generating an adjusted image from the original image upon adjusting a color setting of the original image to align a first color characteristic of the first shade of red in the adjusted image to the first true color characteristic and to align a second color characteristic of the second shade of red in the adjusted image to the second true color characteristic S160"; extracting a redness value from a region of the adjusted image corresponding to a portion of the canister based on a position of the color grid relative to the canister S170"; and correlating the redness value with a concentration of the blood component within a volume of fluid contained in the canister S190".

Generally, in this variation, the method 100" normalizes the image of the canister according to color values of one or more color elements in the image and corresponding reference color values of the color elements. In particular, rather than matching a color value of a color element in the color grid in the image to a color in a selected region of the image corresponding to fluid in the canister, this variation of the method immediately color normalizes the image according to the imaged and reference color values of one or more color elements in the grid, and then implements a parametric model to extrapolate a blood component concentration in the fluid in the imaged canister, as described in relation to the processing system in Section 2 above.

In particular, in this variation, Blocks S150" and S152" can implement methods and techniques similar to those of Blocks S140' and S150' described above to retrieve true color characteristics corresponding to a first shade of red and a second shade of red in the set of distinct shades of red in the original image based on a position of the first shade of red in the color grid in the original image. Alternatively, Block S150" and S152" can retrieve true color values of a red color element and a black color element in the color grid in the image of the canister. However, Blocks S150" and S152" can retrieve any other true color value of one or more color elements in the color grid.

In this variation, Blocks S160", S170", and S190" can then implement methods or techniques similar to Blocks of the foregoing variation to adjust the image, to extract a redness value from a region of the adjusted image corresponding to fluid in the canister, and to correlate the redness value with a concentration of the blood component within a volume of fluid contained in the canister.

Furthermore, as noted above, variations of the method 100" can be adapted to process image data (or other data) derived from any other suitable fluid receiver (e.g., canister, test strip, absorbent pad, surgical textile, sponge, fluid receiving bag, drape, cell salvage system, drain device, etc.) associated with or otherwise coupled to a color grid (e.g., incorporated into a quick response code, incorporated into a barcode, incorporated into a rectilinear array, incorporated into an axially symmetric array, etc.), wherein the fluid receiver is configured to receive (e.g., receive into a cavity, receive upon absorption) a volume of fluid (e.g., urine, saline, ascites, bile, irrigant saliva, gastric fluid, mucus, pleural fluid, interstitial fluid, fecal matter, etc.). In particular, color elements of the color grid, as described above, can comprise any other suitable (e.g., non-red) color(s) configured to facilitate image data normalization for environmental condition effects, and/or for extraction of relevant fluid component characteristics (e.g., concentrations, purities, etc.) from a volume of fluid at the fluid receiver.

Figure 7C:
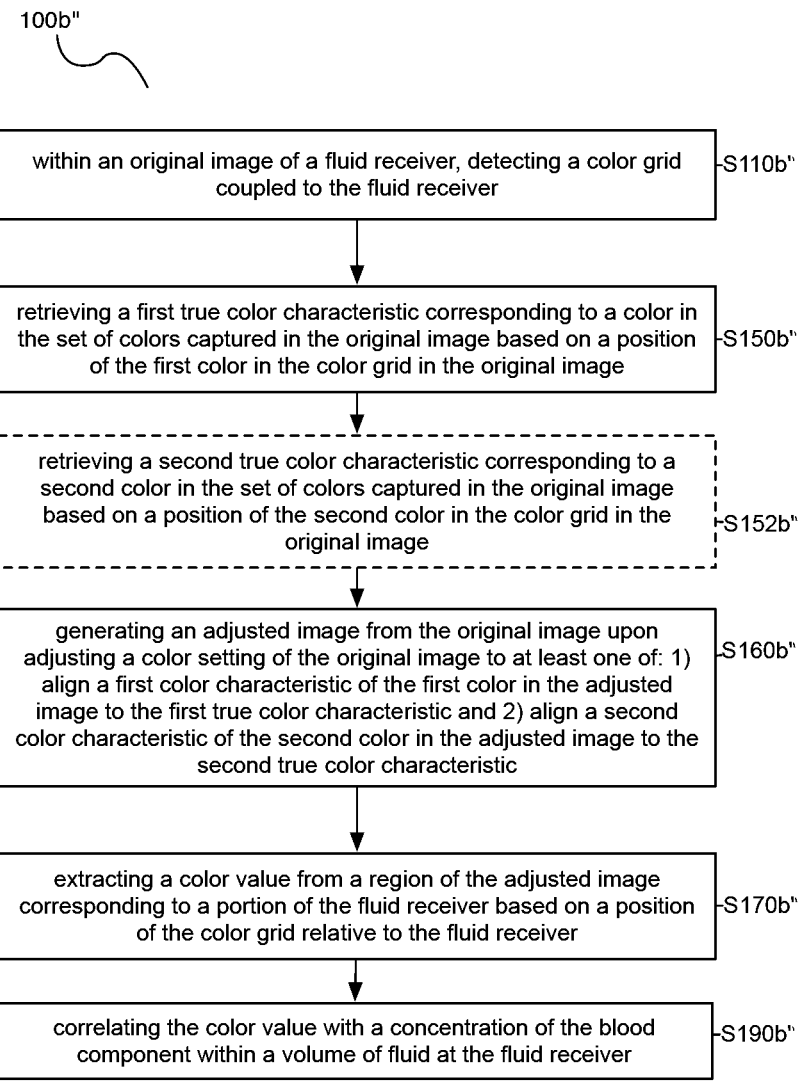

In one such variation, as shown in FIG. 7C, a method 100b" includes: within an original image of a fluid receiver, detecting a color grid coupled to the fluid receiver S110b", the color grid comprising an array of color elements, wherein each color element is associated with at least one of a set of colors; retrieving a first true color characteristic corresponding to a color in the set of colors captured in the original image based on a position of the first color in the color grid in the original image S150b"; retrieving a second true color characteristic corresponding to a second color in the set of colors captured in the original image based on a position of the second color in the color grid in the original image S152b"; generating an adjusted image from the original image upon adjusting a color setting of the original image to align a first color characteristic of the first color in the adjusted image to the first true color characteristic and to align a second color characteristic of the second color in the adjusted image to the second true color characteristic S160b"; extracting a color value from a region of the adjusted image corresponding to a portion of the fluid receiver based on a position of the color grid relative to the fluid receiver S170b"; and correlating the color value with a concentration of the blood component within a volume of fluid at the fluid receiver S190b".

As such, variations of the method 100" can facilitate mitigation of ambient light effects (and other effects) in an environment of the fluid receiver, in determining a concentration and/or an amount of a fluid component within a volume of fluid received at the fluid receiver.

6. Noise Removal and Blood Component Amount

As shown in FIG. 3E, the method 100 can additionally include Block S50, which recites: removing image artifacts present in image data associated with at least one of the canister and the color grid, which functions to improve outputs of subsequent blocks of the method 100. In particular, Block S50 can function to remove noise or other artifacts (e.g., artifacts caused by air bubbles under the color grid, artifacts caused by debris between the color grid 300 and the canister, etc.) from the image data of the region of interest for blood component analysis. In variations, Block S50 can comprise implementing one or more of: a maximally stable extremal regions (MSER) algorithm, a Laplacian of Gaussian algorithm, a difference of Gaussians algorithm, and a determinant of Hessian algorithm, and any other suitable algorithm to remove noise or other artifacts. In a specific example, as described in relation to the processing system of Section 2 above, artifact removal in Block S50 can comprise implementing a maximally stable extremal regions (MSER) algorithm to determine an initial mask of substantially artifact-less subregions of the region of interest. Then, Block S50 can comprise removing any pixels whose color value is significantly different from a median color value of pixels of the initial mask, in order to remove aberrations present after implementation of the MSER algorithm. Variations of Block S50 can, however, be performed in any other suitable manner.

Figure 8:
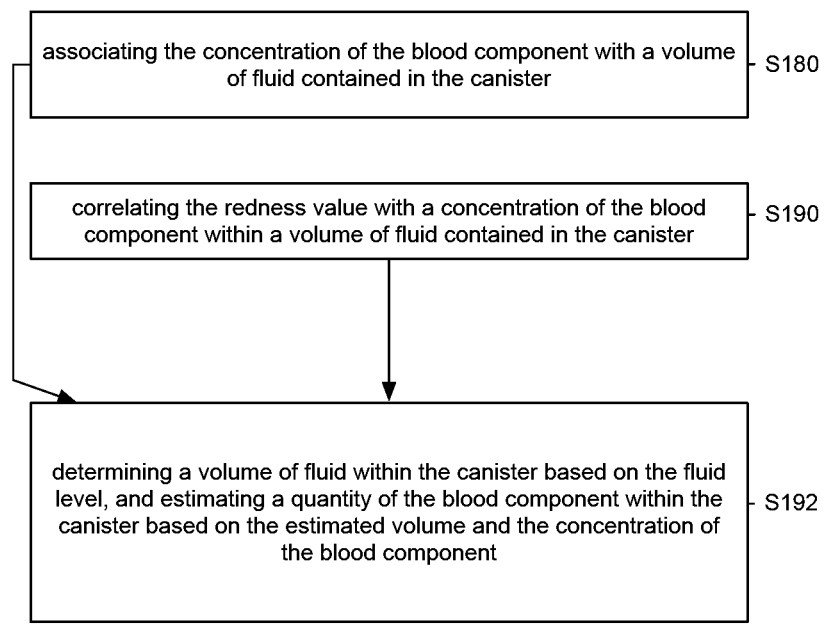
FIG. 8 depicts additional blocks in an embodiment of a method for estimating a quantity of a fluid component.

As shown in FIG. 8, the method 100 can additionally include Block S192, which recites: within an image of a canister, identifying a reference marker on the canister, selecting an area of the image based on the reference marker, correlating a portion of the selected area with a fluid level within the canister, estimating a volume of fluid within the canister based on the fluid level, and estimating a quantity of the blood component within the canister based on the estimated volume and the concentration of the blood component. Alternatively, Block S192 can comprise receiving information pertaining to the volume of fluid within the canister by an entity interacting with the system. In a first variation, the volume of fluid within the canister can be manually input (e.g., with keypad strokes, by speech, etc.) into an input module of a computing device of the system. In an example of the first variation, a holistic blood loss management application executing at a mobile computing device (e.g., tablet computer, smartphone device, etc.) can include a user interface configured to receive an input indicative of the volume of fluid within the canister, wherein the input is provided by a physician, nurse, assistant, or technician present within an operating room environment. In the example, the Block S192 can thus use the input volume of fluid information in estimating a quantity of the blood component within the canister. However, in alternative variations and examples, the quantity of the blood component within the canister can be determined in any other suitable manner.

Additionally or alternatively, Block S192 can implement methods and techniques described in U.S. patent application Ser. No. 14/072,625 to detect the volume of fluid in the canister and to calculate the total volume, mass, weight, or other method of the blood component in the canister based on the total volume and the estimated blood component concentration in the canister.

7. Specific Example Pipeline

Figure 9:
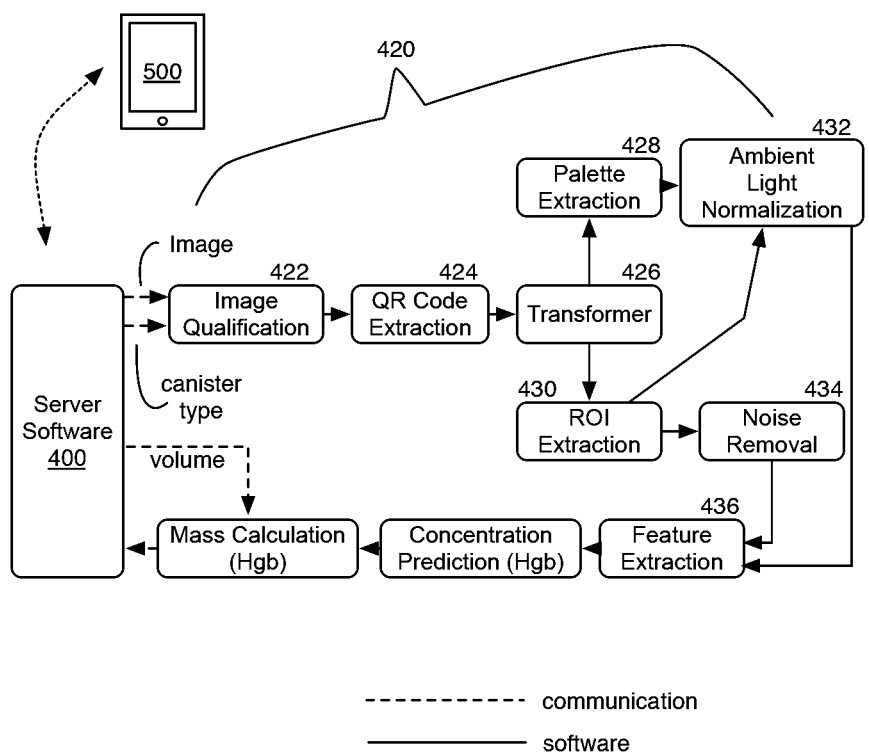
FIG. 9 depicts an example of a system for estimating a quantity of a fluid component.

As shown in FIG. 9, in one specific example of a pipeline associated with the method(s) 100, 100b, 100', 100b', 100", 100b" and implementing an embodiment of the described system: software executing on a server 400, in communication with a mobile computing device 500 that captures the image of the canister and color grid, can facilitate transmission of image and canister type data to a processing module 420 (e.g., computing subsystem) for estimation of the amount of the blood component within a fluid canister. The processing module 420 can include a first module 422 configured to perform image qualification algorithms (e.g., image processing algorithms, image conditioning algorithms, etc.), and configured to provide an output to a second module 424 configured to extract information from a matrix barcode (e.g., QR code-color grid hybrid, in relation to Block S110 above) captured in the image. The information from the matrix barcode can then be passed through a transformation module 426, that implements a transformation from canonical space to image space (e.g., based upon a template of how the matrix barcode should look in a known configuration), to a third module 428 for extraction of ambient light palette information (i.e., in relation to Block S150 above) and a fourth module 430 for processing of information related to a region of interest (i.e., in relation to Block S120 above). Outputs of the third module 428 and the fourth module 430 are then transmitted to an ambient light normalization module 432 configured to generate a corrected image from the original image, wherein the corrected image is normalized in a manner that accounts for variations in ambient light conditions. An output of the third module 428 is also transmitted to a noise filtering module 434 configured to mitigate effects of noise in the image. Then, outputs of the ambient light normalization module 432 and the noise filtering module 434 are transmitted to a feature extraction module 436 (e.g., in relation to Blocks S140, S170, and S190 above) in order to retrieve an estimated hemoglobin concentration associated with the region of the image and representative of the hemoglobin concentration of fluid within the canister. Finally, the estimated hemoglobin concentration and an estimated volume of fluid within the canister (e.g., in relation to Block S192 above) are used to calculate a mass of hemoglobin within the canister, which is then transmitted back to the server 400 (e.g., and eventually provided to an entity associated with a patient from whom the blood originated). Variations of the specific example can, however, be implemented in any other suitable manner.

The systems and methods of the preferred embodiment can be embodied and/or implemented at least in part as a machine configured to receive a computer-readable medium storing computer-readable instructions. The instructions are preferably executed by computer-executable components preferably integrated with the application, applet, host, server, network, website, communication service, communication interface, hardware/firmware/software elements of a user computer or mobile device, or any suitable combination thereof. Other systems and methods of the preferred embodiment can be embodied and/or implemented at least in part as a machine configured to receive a computer-readable medium storing computer-readable instructions. The instructions are preferably executed by computer-executable components preferably integrated by computer-executable components preferably integrated with apparatuses and networks of the type described above. The computer-readable medium can be stored in the cloud and/or on any suitable computer readable media such as RAMs, ROMs, flash memory, EEPROMs, optical devices (CD or DVD), hard drives, floppy drives, or any suitable device. The computer-executable component is preferably a processor but any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGS. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention as defined in the following claims.

We claim:

1. A method for assessing concentration of a fluid component within a container, comprising:
   at a computing system in communication with an image acquisition device, receiving data associated with an image of the container generated by the image acquisition device;
   detecting a color grid in the image, the color grid comprising an array of color elements, wherein each color element of the color grid is associated with at least one of a set of colors;
   generating an adjusted image by adjusting a color setting in the image to align a color characteristic of a first color in the set of colors to a true color characteristic of the first color; and
   determining a concentration of the fluid component based on a region of the adjusted image associated with the container.

2. The method of claim 1, wherein detecting the color grid comprises detecting corner features of the color grid.

3. The method of claim 2, wherein detecting the color grid further comprises: fitting a homography between canonical space and an image space associated with the image; and with the homography, transforming each of a set of regions associated with a color element of the color grid from canonical space to the image space.

4. The method of claim 1, further comprising at the computing system, determining the true color characteristic based upon a position of the first color in the color grid in the image.

5. The method of claim 4, wherein the true color characteristic is determined from a reference dataset of the color grid, and wherein generating the adjusted image comprises adjusting at least one component color setting of the image to align the color characteristic of the first color to the first true color characteristic of the first color.

6. The method of claim 5, further comprising generating a fit parameter derived from alignment of the color characteristic to the true color characteristic; and providing an indication of suitability of the image, based upon the fit parameter.

7. The method of claim 1, wherein determining the concentration of the fluid component comprises determining the concentration from a set of color parameters derived from the region of the adjusted image.

8. The method of claim 7, wherein determining the concentration from the set of color parameters comprises transforming at least one color component into a concentration representative of the region of the adjusted image.

9. The method of claim 8, further comprising determining an amount of the fluid component within the container, the amount derived from the concentration multiplied by the volume of fluid within the container.

10. A method for assessing concentration of a fluid component received at a fluid receiver, the method implemented at a computer system and comprising:
    receiving data associated with an image of the fluid receiver;
    detecting a color grid in the image, the color grid comprising an array of color elements in proximity to the fluid receiver, wherein each color element of the color grid is associated with at least one of a set of colors;
    generating an adjusted image by adjusting a color setting in the image to align a color characteristic of a first color in the set of colors to a true color characteristic of the first color; and
    determining a concentration of the fluid component based on a region of the adjusted image associated with the container.

11. The method of claim 10, wherein receiving data associated with an image of the fluid receiver comprises receiving data associated with the image of at least one of: a canister, a test strip, an absorbent pad, a surgical textile, a sponge, a fluid receiving bag, a drape, a cell salvage system, and a drain device.

12. The method of claim 11, wherein detecting the color grid comprises: detecting a positional feature of the color grid; determining an identifier of the fluid receiver upon decoding information from the color grid; and retrieving a template of the color grid in canonical space upon reception of the identifier.

13. The method of claim 12, further comprising: determining the true color characteristic of the first color in the set of colors captured in the image, based upon a position of the first color in the color grid in the image, wherein the true color characteristic is determined from a reference dataset of the color grid, and wherein generating the adjusted image comprises adjusting at least one of a red component color setting, a green component color setting, and a blue component color setting of the image to align the color characteristic of the first color to the first true color characteristic of the first color.

14. The method of claim 10, wherein determining the concentration of the fluid component based on the region of the adjusted image comprises at least one of 1) associating a color value of the region of the adjusted image with a color element of the color grid, wherein the color element of the color grid is associated with a predetermined concentration of the fluid component; and 2) generating a set of color parameters from the region of the adjusted image, and determining the concentration of the fluid component based upon a parametric model that receives the set of color parameters as inputs.

15. The method of claim 14, further comprising removing noise from the region of the adjusted image based upon an algorithm configured remove any pixels from the region whose color value is significantly different from a median color value of pixels of the region.

16. The method of claim 11, wherein determining the concentration of the fluid component from the region of the adjusted image comprises determining the concentration from a set of color parameters derived from the region of the adjusted image, the set of color parameters including a red component, a green component, and a blue component.

17. The method of claim 16, wherein determining a concentration of the fluid component from the region comprises determining the concentration of a bodily fluid component derived from at least one of: urine, saline, ascites, bile, irrigant saliva, gastric fluid, mucus, pleural fluid, interstitial fluid, and fecal matter.

18. A system for assessing an amount of a fluid component, the system comprising:
 a fluid receiver and a color grid comprising an array of color elements in proximity to the fluid receiver, wherein each color element of the color grid is associated with at least one of a set of colors;
 an image acquisition device configured to capture an image of the fluid receiver and the color grid within a window of view; and
 a computing system in communication with the image acquisition device and comprising:
  a first module configured to detect the color grid within the image;
  a second module configured to determine a first true color characteristic of a first color in the set of colors captured in the image, based upon a position of the first color in the color grid in the image;
  a third module configured to generate an adjusted image by adjusting a color setting of the image to align a first color characteristic of the first color to the first true color characteristic of the first color;
  a fourth module configured to determine a concentration of the fluid component from a region of the adjusted image corresponding to a portion of the fluid receiver; and
  a fifth module configured to generate an analysis indicative of the amount of the fluid component at the fluid receiver, based upon the concentration of the fluid component and a volume of fluid received at the fluid receiver.

19. The system of claim 18, wherein the image acquisition device comprises a display configured to render fluid component amount information, derived from the analysis.

20. The system of claim 19, wherein the fluid receiver comprises a canister configured to receive fluid including a blood component, wherein the color grid is integrated with a quick response code including the array of color elements, and wherein the computing system is configured to decode an identifier of the canister from the quick response code.

21. The system of claim 18, wherein the fourth module of the computing system is configured to determine a hemoglobin concentration associated with the region, upon processing a red color component, a green color component, and a blue color component of the region with a parametric model, and wherein the fifth module of the computing system is configured to determine a hemoglobin mass associated with the volume of fluid received at the fluid receiver.

* * * * *